United States Patent
Li et al.

(10) Patent No.: US 11,040,965 B2
(45) Date of Patent: Jun. 22, 2021

(54) PROCESS FOR MAKING HEPATITIS B CORE PROTEIN MODULATORS

(71) Applicant: Assembly Biosciences, Inc., South San Francisco, CA (US)

(72) Inventors: Leping Li, Carmel, IN (US); Lee D. Arnold, Bloomington, IN (US); Sreenivasa Reddy Mundla, Hyderabad (IN)

(73) Assignee: Assembly Biosciences, Inc., South San Francisco, CA (US)

( * ) Notice: Subject to any disclaimer, the term of this patent is extended or adjusted under 35 U.S.C. 154(b) by 0 days.

(21) Appl. No.: 16/493,614

(22) PCT Filed: Mar. 13, 2018

(86) PCT No.: PCT/US2018/022100
§ 371 (c)(1),
(2) Date: Sep. 12, 2019

(87) PCT Pub. No.: WO2018/169907
PCT Pub. Date: Sep. 20, 2018

(65) Prior Publication Data
US 2020/0002325 A1  Jan. 2, 2020

Related U.S. Application Data

(60) Provisional application No. 62/470,560, filed on Mar. 13, 2017.

(51) Int. Cl.
| | |
|---|---|
| C07D 417/12 | (2006.01) |
| C07C 231/10 | (2006.01) |
| C07C 231/12 | (2006.01) |
| C07C 315/02 | (2006.01) |
| C07C 315/04 | (2006.01) |
| C07C 319/14 | (2006.01) |
| C07C 319/20 | (2006.01) |

(52) U.S. Cl.
CPC .......... *C07D 417/12* (2013.01); *C07C 231/10* (2013.01); *C07C 231/12* (2013.01); *C07C 315/02* (2013.01); *C07C 315/04* (2013.01); *C07C 319/14* (2013.01); *C07C 319/20* (2013.01)

(58) Field of Classification Search
CPC .................................................. C07D 417/12
See application file for complete search history.

(56) References Cited

U.S. PATENT DOCUMENTS

| | | | |
|---|---|---|---|
| 5,512,563 A | 4/1996 | Albright et al. | |
| 8,618,090 B2 | 12/2013 | Desai et al. | |
| 9,399,619 B2 | 7/2016 | Guo et al. | |
| 9,873,684 B2 | 1/2018 | Kahraman et al. | |
| 10,377,748 B2 | 8/2019 | Turner et al. | |
| 10,392,379 B2 | 8/2019 | Turner et al. | |
| 2007/0105819 A1 | 5/2007 | Olsson et al. | |
| 2007/0105835 A1 | 5/2007 | Kazantsev | |
| 2015/0368261 A1 | 12/2015 | Demin et al. | |
| 2017/0015658 A1* | 1/2017 | Turner, Jr. | C07D 413/12 |
| 2017/0107185 A1 | 4/2017 | Grammneos et al. | |
| 2017/0267685 A1 | 9/2017 | D'Agostino et al. | |
| 2018/0265484 A1 | 9/2018 | Turner et al. | |

FOREIGN PATENT DOCUMENTS

| | | |
|---|---|---|
| CL | 2015002706 A1 | 4/2016 |
| CL | 2015003456 A1 | 7/2016 |
| CL | 20105002628 | 8/2016 |
| CL | 2016003175 A1 | 8/2017 |
| CN | 103889953 B | 6/2016 |
| CN | 106413402 A | 2/2017 |
| GB | 1480553 A | 7/1977 |
| JP | 58225074 | 12/1983 |
| JP | 2018-531918 A | 11/2018 |
| WO | WO-92/19277 A1 | 11/1992 |
| WO | WO-2005/072741 A1 | 8/2005 |
| WO | WO-2007/105819 A1 | 9/2007 |
| WO | WO-2008/036139 A3 | 12/2008 |
| WO | WO-2008/118141 A3 | 12/2008 |
| WO | WO-2010/011537 A1 | 1/2010 |
| WO | WO-2012/045194 A1 | 4/2012 |
| WO | WO-2013/006394 A1 | 1/2013 |
| WO | WO-2015/017412 A1 | 2/2015 |
| WO | 2015138895 A1 | 9/2015 |
| WO | WO-2017/048954 A1 | 3/2017 |
| WO | WO-2017048962 A1 | 3/2017 |

OTHER PUBLICATIONS

Supplemental European Search Report issued by the European Patent Office (Munich), dated Apr. 11, 2018, for related Application No. EP 15761201; 21 pages.

Supplemental Partial European Search Report issued by the European Patent Office (Munich), dated Nov. 23, 2017, for related Application No. EP 15761201; 14 pages.

Takeda, M., et al., "Synthesis of Dibenzo (b,e) [1,4] Diazepine Derivatives as Anti-depressants," Yakugaku Zahhi, vol. 89, No. 2, (1969), 6 pages.

(Continued)

*Primary Examiner* — Bruck Kifle
(74) *Attorney, Agent, or Firm* — Goodwin Procter LLP

(57) ABSTRACT

The present disclosure provides, in part, a process for preparing compounds (I) having allosteric effector properties against Hepatitis B virus Cp.

Formula I

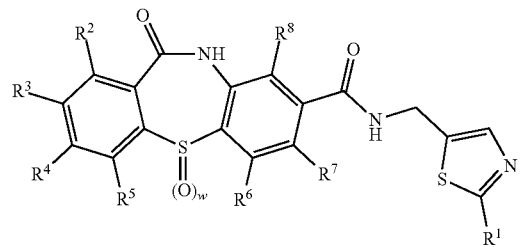

17 Claims, No Drawings

(56) References Cited

OTHER PUBLICATIONS

National Center for Biotechnology Information, PubChem Compound Database; CID-4152425, XP-002779931, modified Apr. 7, 2017, created Sep. 13, 2005; 3 pages.
National Center for Biotechnology Information, PubChem Compound Database; CID-46260649, XP-002779932, modified Apr. 7, 2017, created Jul. 21, 2010; 3 pages.
National Center for Biotechnology Information, PubChem Compound Database; CID-4163919, XP-002779933, modified Apr. 7, 2018, created Sep. 13, 2005; 3 pages.
National Center for Biotechnology Information, PubChem Compound Database; CID-4167865, XP-002779934, modified Apr. 7, 2018, created Sep. 13, 2005; 3 pages.
National Center for Biotechnology Information, PubChem Compound Database; CID-4338109, XP-002779935, modified Apr. 7, 2018, created Sep. 14, 2005; 3 pages.
National Center for Biotechnology Information, PubChem Compound Database; CID-4163918, XP-002779936, modified Apr. 7, 2018, created Sep. 13, 2005; 3 pages.
National Center for Biotechnology Information, PubChem Compound Database; CID-3576843, XP-002779937, modified Apr. 7, 2018, created Sep. 9, 2005; 3 pages.
National Center for Biotechnology Information, PubChem Compound Database; CID-4577044, XP-002779938, modified Apr. 7, 2018, created Sep. 15, 2005; 3 pages.
National Center for Biotechnology Information, PubChem Compound Database; CID-4097179, XP-002779940, modified Apr. 7, 2018, created Sep. 13, 2005; 3 pages.
National Center for Biotechnology Information, PubChem Compound Database; CID-23797169, XP-002779941, modified Apr. 7, 2018, created Feb. 20, 2008; 3 pages.
National Center for Biotechnology Information, PubChem Compound Database; CID-53384785, XP-002779942, modified Apr. 7, 2018, created Oct. 13, 2011; 3 pages.
National Center for Biotechnology Information, PubChem Compound Database; CID-20885138, XP-002775927, modified Nov. 18, 20187, created Dec. 5, 2007; 3 pages.
National Center for Biotechnology Information, PubChem Compound Database; CID-20885146, XP-002775928, modified Nov. 18, 2017, created Dec. 5, 2007; 3 pages.
National Center for Biotechnology Information, PubChem Compound Database; CID-20885149, XP-002775929, modified Nov. 18, 2017, created Dec. 5, 2007; 3 pages.
National Center for Biotechnology Information, PubChem Compound Database; CID-20885150, XP-002775930, modified Nov. 18, 2017, created Dec. 5, 2007; 3 pages.
National Center for Biotechnology Information, PubChem Compound Database; CID-20885171, XP-002775931, modified Nov. 18, 2017, created Dec. 5, 2007; 3 pages.
Letter Exam Report from the Australian Patent Office, dated May 6, 2018, for Australian Application No. 2015229174; 6 pages.
Office Action issued by the Belize Intellectual Property Office, dated May 18, 2018, for Belize Patent Application No. 887.16; 2 pages.
English translation of the First Official Action issued by the Mexican Patent Office for Mexican Patent Application No. MX/a/2016/011800, dated Jul. 4, 2018; 3 pages.
Letter dated Jun. 27, 2018 regarding Examination Report issued by the National Office of Industrial Property for Dominican Republic Patent Application No. P2016-0233; 2 pages.
Letter Exam Report issued by the Patent Office of the People's Republic of China (translated in English language), dated Jun. 29, 2018, for Chinese Application No. 201580024580.0; (3 pages).
Letter Exam Report issued by the Chilean Patent Office, dated Jun. 12, 2018, for Chilean Application No. 2269-2016; 15 pages.
National Center for Biotechnology Information, PubChem Compound Database; CID-23734106, XP-002779939, modified Apr. 7, 2018, created Feb. 20, 2008; 3 pages.

Hall, Pamela R., et al., "Small molecule inhibitors of hantavirus infection,"Bioorganic & Medicinal Chemistry Letters, vol. 20, (2010), pp. 7085-7091.
Xiao, et al., "Discovery, Optimization, and Characterization of Novel D2 Dopamine Receptor Selective Antagonists," Journal of Medicinal Chemistry, Mar. 25, 2014, vol. 57, pp. 3450-3463.
International Preliminary Report on Patentability issued by the International Bureau of WIPO, dated Sep. 13, 2016, for International Application No. PCT/US2015/020444; 6 pages.
International Search Report and Written Opinion issued by the ISA/US, Commissioner for Patents, dated Jul. 6, 2015, for International Application No. PCT/US2015/020444; 10 pages.
National Center for Biotechnology Information. PubChem Compound Database; CID=20885151; available at https://pubchem.ncbi.nlm.nih.gov/compound/20885151 (accessed Sep. 13, 2016; deposit date Dec. 5, 2007); 10 pages.
National Center for Biotechnology Information. PubChem Compound Database; CID=4 II 9 I71, available at https://pubchem.ncbi.nlm.nih.gov/compound/4119171 (accessed Sep. 13, 2016; deposit date Sep. 3, 2005); 12 pages.
National Center for Biotechnology Information. PubChem Compound Database; CID-4167865, https://pubchem.ncbi.nlm.nih.gov/compound/4167865 (accessed Sep. 13, 2016; deposit date Sep. 13, 2005); 12 pages.
International Preliminary Report on Patentability dated Mar. 20, 2018, for International Application No. PCT/US2016/051934 (6 pages).
International Search Report and Written Opinion dated Dec. 29, 2016 for International Application No. PCT/US16/51934.
International Preliminary Report on Patentability dated Dec. 29, 2016, for International Application No. PCT/US2016/051949.
International Search Report and Written Opinion dated Dec. 29, 2016 for International Application No. PCT/US16/51949.
International Preliminary Report on Patentability dated Oct. 28, 2016, for International Application No. PCT/US2016/051940.
International Search Report and Written Opinion dated Oct. 28, 2016 for International Application No. PCT/US16/51949.
National Center for Biotechnology Information, PubChem Compound Database; CID-201327, create date: Aug. 9, 2005; 3 pages.
Supplementary European Search Report issued for EP16847298, dated Jan. 28, 2019 (6 pages).
Notice of Reasons for Rejection issued for Japanese Patent Application No. 2016-557019, dated Oct. 30, 2018 (6 pages).
Official Office Action issued in Eurasian application No. 201890731, dated Oct. 31, 2018.
Office Action issued by the Belize Intellectual Property Office, dated Nov. 21, 2018, for Belize Patent Application No. 925.18 (3 pages).
Extended European Search Report issued in EP16847298.3, dated Jan. 2, 2019.
Extended European Search Report issued for European Patent Application No. 16847295.9, dated Apr. 15, 2019.
Xiao, et al.. "Discovery, Optimization, and Characterization of Novel D2 Dopamine Receptor Selective Antagonists", Journal of Medicinal Chemistry, vo. 57, p. 3450-63 (2014).
Office Action issued by the Chinese Intellectual Property Office, dated Mar. 17, 2020, for Chinese Patent Application No. 201680065139.1.
Ito, et. al. "A Medium-Term Rat Liver Bioassay for Rapid in Vivo Detection of Carcinogenic Potential of Checmicals," Cancer Sci, Jan. 2003, vol. 94, pp. 3-8.
STN Registry Database Entry for CAS RN688762_67_6—Jun. 3, 2004, Accessed Aug. 8, 2019.
Ito et al. in Cancer Science 94(1), 3-8 (2003).
STN Registry database entry for CAS RN 688762-67-6, Entered STN Jun. 3, 2004, Accessed Aug. 8, 2019.
European Search Report and Search Opinion Received for EP Application No. 16847295.9, dated Apr. 15, 2019, 6 pages.
European Search Report and Search Opinion Received for EP Application No. 16847298.3, dated Feb. 1, 2019, 7 pages.
European Search Report and Search Opinion Received for EP Application No. 16847305.6, dated Mar. 26, 2019, 8 pages.
Pubchem CD 201327; Aug. 9, 2005.

(56) References Cited

OTHER PUBLICATIONS

English translation of the Third Office Action, issued by the National Intellectual Property Administration of the People's Republic of China, dated Dec. 2, 2019, for Chinese Patent Application No. 201580024580.0.
English translation of Examination Report issued by the State of Israel Ministry of Justice, The Patent Office, dated Mar. 7, 2019, for Israeli Patent Application No. 247575.
Notification of Written Opinion issued by the Intellectual Property Office Brunei Darussalam, dated Feb. 25, 2019, or Brunei Patent Application No. BN/N/2016/0072.
Invitation to Respond to Written Opinion issued the by the Intellectual Property Office of Singapore, dated May 22, 2019, for Singapore Patent Application No. 11201802110X.
Examination Report issued by the Government of India, Intellectual Property India, dated Feb. 27, 2020, for Indian latent Application No. 201817014105.
Examination Report issued by the National Institute of Industrial Property—INAPI—Expert Response on Invention Patent Application, dated Jan. 15, 2020, for Chilean Patent Application No. 201800684.
Wahome et al., "Identification of Small Molecules That Suppress Ricin-Induced Stress-Activated Signaling Pathways," PLOS One, Nov. 2012, vol. 7, No. 11.
Patani, George A., et al. "Bioisosterism: A Rational Approach in Drug Design", Chemical Reviews, vol. 96, No. 8, Jan. 1, 1996, pp. 3147-3176, XP055573925.
Summary dated Jun. 28, 2019 of Examination Report issued by the Indonesia Patent Office for Indonesian Patent Application No. P-00 2016 06767.
English translation of Examination Report issued by the State of Israel Ministry of Justice, The Patent Office, dated Jul. 8, 2019, for Israeli Patent Application No. 247575.
English translation of Official Action issued by the Uzbekistan Patent Office, dated May 6, 2019, for Patent Application No. AP20160428.
Office Action issued by the Patent Authority of the State of Israel, Ministry of Justice, dated Mar. 9, 2020, for Israeli Patent Application No. 258124.

International Search Report and Written Opinion dated Oct. 28, 2016 for International Application No. PCT/US2016/051940.
Office Action issued by the Canadian Intellectual Property Office, dated Sep. 16, 2019, for Canadian Patent Application No. 2,942,533.
Office Action issued by the Canadian Intellectual Property Office, dated Feb. 1, 2019, for Canadian Patent Application No. 2,942,533.
Extended European Search Report issued by the European Patent Office, Munich, Germany, dated Feb. 13, 2020, for European Patent Application No. 19184535.3.
Partial European Search Report issued by the European Patent Office, Munich Germany, dated Nov. 11, 2019, or European Patent Application No. 19184535.3.
Office Action and Search Report issued by the National Institute of Industrial Property, dated Jan. 15, 2020, for Chilean Patent Application No. 201800684.
Office Action issued by the National Institute of Industrial Property, dated Sep. 11, 2019, for Chilean Patent Application No. 201800684.
Office Action issued by the Eurasian Patent Organization dated Oct. 2, 2018, for Eurasian Application No. 201890731/28.
English translation of the Second Office Action, issued by the National Intellectual Property Administration of the People's Republic of China, dated Mar. 19, 2019, for Chinese Patent Application No. 201580024580.0.
English translation of Office Action issued by the Japanese Patent Office, dated Oct. 30, 2018, for Japanese Patent Application No. 2016-557019.
Office Action issued by the Japanese Patent Office, dated Apr. 7, 2020, for Japanese Patent Application No. 2019-085742; 2 pages.
Restriction issued by the Intellectual Property Office of the Philippines Bureau of Patents, dated Jun. 1, 2020, for Application No. 1/2016/501762; 21 pages.
Takehiko Nishio et al., "Thionation of[omega]- Acylamino Ketones with Lawesson's Reagent: Convenient Synthesis of 1,3-Thiazoles and 4H-1,3-Thiazines," Helvetica Chimica Acta, vol. 84, No. 8, (2001), pp. 2347-2354.
Examination Report, issued in IN Application No. 201917038714, dated Apr. 19, 2021.

* cited by examiner

PROCESS FOR MAKING HEPATITIS B CORE PROTEIN MODULATORS

RELATED APPLICATION

This application is a national stage entry of international patent application number PCT/US2018/022100 filed on Mar. 13, 2018 which claims priority to and the benefit of U.S. provisional application No. 62/470,560, filed on Mar. 13, 2017, each of which is incorporated by reference in its entirety.

BACKGROUND

Hepatitis B (HBV) causes viral hepatitis that can further lead to chronic liver disease and increase the risk of liver cirrhosis and liver cancer (hepatocellular carcinoma). Worldwide, about 2 billion people have been infected with HBV, around 360 million people are chronically infected, and every year HBV infection causes more than one half million deaths. HBV can be spread by body fluids: from mother to child, by sex, and via blood products. Children born to HBV-positive mothers may also be infected, unless vaccinated at birth.

The hepatitis virus particle is composed of a lipid enveloped studded with surface protein (HBsAg) that surrounds the viral core. The core is composed of a protein shell, or capsid, built of 120 core protein (Cp) dimers, which in turn contains the relaxed circular DNA (rcDNA) viral genome as well as viral and host proteins. In an infected cell, the genome is found as a covalently closed circular DNA (cccDNA) in the host cell nucleus. The cccDNA is the template for viral RNAs and thus viral proteins. In the cytoplasm, Cp assembles around a complex of full-length viral RNA (the so-called pregenomic RNA or pgRNA and viral polymerase (P). After assembly, P reverse transcribes the pgRNA to rcDNA within the confines of the capsid to generate the DNA-filled viral core.

At present, chronic HBV is primarily treated with nucleos(t)ide analogs (e.g. entecavir) that suppress the virus while the patient remains on treatment but do not eliminate the infection, even after many years of treatment. Once a patient starts taking nucleotide analogs most must continue taking them or risk the possibility of a life threatening immune response to viral rebound. Further, nucleos(t)ide therapy may lead to the emergence of antiviral drug resistance.

The only FDA approved alternative to nucleos(t)ide analogs is treatment with interferon α or pegylated interferon α. Unfortunately, the adverse event incidence and profile of interferon α can result in poor tolerability, and many patients are unable to complete therapy. Moreover, only a small percentage of patients are considered appropriate for interferon therapy, as only a small subset of patients are likely to have a sustained clinical response to a course of interferon therapy. As a result, interferon based therapies are used in only a small percentage of all diagnosed patients who elect for treatment.

Thus, current HBV treatments can range from palliative to watchful waiting. Nucleos(t)ide analogs suppress virus production, treating the symptom, but leave the infection intact. Interferon α has severe side effects and less tolerability among patients and is successful as a finite treatment strategy in only a small minority of patients. Accordingly, there is a clear on-going need for more effective processes for making compounds capable of treating viral infections, for example, hepatitis B.

SUMMARY

The present disclosure provides, for example, a process for preparing hepatitis B core protein modulators, e.g., a process for preparing compounds which may have allosteric effector properties against Hepatitis B virus Cp, a protein found as a dimer, a multimer, and as the protein shell of the HBV core. For example, provided herein is a process for preparing compounds which may be useful for treating viral infections, such as hepatitis B.

In certain embodiments, provided herein is a process for preparing a compound of Formula I:

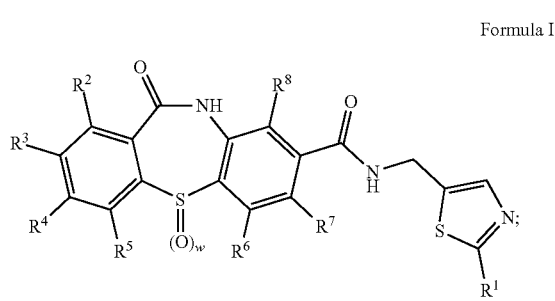

Formula I wherein w, $R^1$, $R^2$, $R^3$, $R^4$, $R^5$, $R^6$, $R^7$, and $R^8$ are as defined below.

In certain other embodiments, provided herein is a process for preparing a compound of Formula VIII:

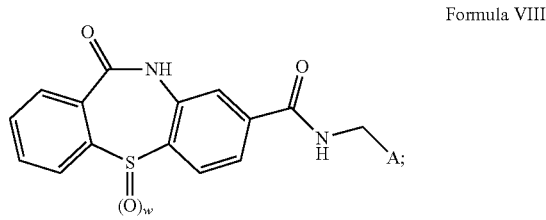

Formula VIII wherein w and A are as defined below.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

As intended herein, the terms "a" and "an" include singular as well as plural references unless the context clearly dictates otherwise.

The term "alkyl" as used herein refers to a saturated straight or branched hydrocarbon. Exemplary alkyl groups include, but are not limited to, straight or branched hydrocarbons of 1-6, 1-4, 1-3 or 2-6 carbon atoms, referred to herein as $C_{1-6}$alkyl, $C_{1-4}$alkyl, $C_{1-3}$alkyl, and $C_{2-6}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated 4-7 membered ring structures, whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc The terms "hydroxy" and "hydroxyl" as used herein refers to the radical —OH.

"Treatment" as used herein includes the alleviation, prevention, reversal, amelioration or control of a pathology, disease, disorder, process, condition or event, including viral infection. In this context, the term "treatment" is further to be understood as embracing the use of a drug to inhibit, block, reverse, restrict or control progression of viral infection.

As used herein, the term "pharmaceutical composition" refers to compositions of matter comprising at least one pharmaceutical compound and optionally a pharmaceutically acceptable carrier.

As used herein, the term "pharmaceutical compound" or "drug" refers to a free compound, its therapeutically suitable salts, solvates such as hydrates, specific crystal forms of the compound or its salts, or therapeutically suitable prodrugs of the compound.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The compounds of the disclosed process may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosed process may contain one or more double bonds and, therefore, exist as geometric isomers resulting from the arrangement of substituents around a carbon-carbon double bond. The symbol ⁓ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

The compounds of the disclosed process may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the disclosed process can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds of the disclosed process can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the disclosed process which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled compounds of the disclosed process (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "therapeutically suitable salt," refers to salts or zwitterions of pharmaceutical compounds which are water or oil-soluble or dispersible, suitable for treatment of disorders and effective for their intended use. The salts may be prepared, for instance, during the final isolation and purification of the compounds or separately by reacting an amino group of the compounds with a suitable acid. For example, a compound may be dissolved in a suitable solvent, such as but not limited to methanol and water, and treated with at least one equivalent of an acid, for instance hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of a compound may also be quaternized with alkyl chlorides, bromides, and iodides such as methyl, ethyl, propyl, isopropyl, butyl, lauryl, myristyl, stearyl, and the like.

Basic addition salts may be prepared, for instance, during the final isolation and purification of pharmaceutical compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts may derived, for example, from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like.

The term "therapeutically suitable prodrug," refers to those prodrugs or zwitterions which are suitable for use in contact with the tissues of subjects and are effective for their intended use. The term "prodrug" refers to compounds that are transformed in vivo to a pharmaceutical compound, for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The terms "pharmaceutically effective amount" and "effective amount", as used herein, refer to an amount of a pharmaceutical formulation that will elicit the desired therapeutic effect or response when administered in accordance with the desired treatment regimen.

The term "modulating" encompasses, fore example, increasing, enhancing, inhibiting, decreasing, and suppressing. The terms "increasing" and "enhancing" mean to cause a net gain by either direct or indirect means. As used herein, the terms "inhibiting" and "decreasing" encompass causing a net decrease by either direct or indirect means.

Without being bound by theory, compounds of the disclosed process may ultimately target multimerization of viral core proteins, which is central to HBV infection, where the core protein multimerizes into shell, or capsid, and/or compounds of the disclosed process may for example, ultimately target interaction of viral core proteins with other macromolecules, such as host or viral nucleic acid, host proteins, or other viral proteins. For example, compounds of the disclosed process may be considered in some embodiments CpAM—core protein allosteric modifiers. CpAM interaction with core protein can allosterically favor an assembly-active form of Cp dimer and lead to viral capsid assembly at an inappropriate time or place or lead to non-standard intersubunit interactions, all resulting in defective capsids. CpAMs may additionally or alternatively affect steps of "upstream" of capsid assembly by altering the concentrations or nature of Cp available as dimer as compared to capsid or other multimeric forms. Compounds of the disclosed process or CpAMs may, in some embodiments, noticeably affect functions upstream of viral assembly such as modulation of covalently closed circular DNA (cccDNA) transcription, RNA stability and/or protein-protein interactions.

Hepatitis B Core Protein Modulators

In one embodiment, provided herein is a process for preparing a compound represented by Formula I:

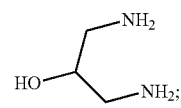

Formula I wherein w is 0, 1, or 2;

$R^1$ is selected from the group consisting of $C_{1-6}$alkyl (optionally substituted with one, two or three halogens), phenyl, and 4-6 membered monocyclic heteroaryl; wherein phenyl and 4-6 membered monocyclic heteroaryl may optionally be substituted with one or more substituents each independently selected from $R^{11}$;

$R^{11}$ is selected from the group consisting of hydrogen, halogen, cyano, $C_{1-6}$alkyl, $C_{1-6}$alkoxy, and —S(O)$_w$—$C_{1-6}$alkyl (wherein w is 0, 1 or 2);

$R^2$, $R^3$, $R^4$, $R^5$, $R^6$, $R^7$, and $R^8$ are each independently selected from the group consisting of hydrogen, halogen, $C_{1-6}$alkyl, and $C_{1-6}$alkoxy; wherein $C_{1-6}$alkyl and $C_{1-6}$alkoxy may be optionally substituted with one, two, three or more substituents each independently selected from the group consisting of halogen, hydroxyl, and $C_{1-6}$alkoxy;

comprising:

amidating a compound of Formula II:

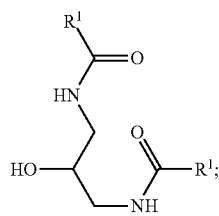

Formula II to provide a compound of Formula III:

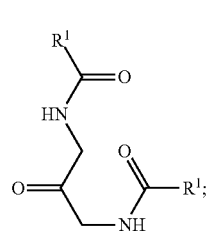

Formula III oxidizing the compound of Formula III to provide a compound of Formula IV:

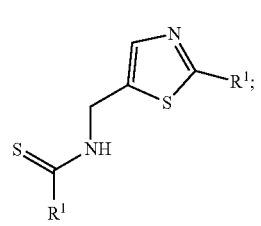

Formula IV cyclizing the compound of Formula IV to provide a thiazole compound of Formula V:

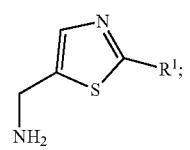

Formula V hydrolyzing the compound of Formula V to provide a compound of Formula VI:

Formula VI and coupling the compound of Formula VI with a tricyclic compound of Formula VII:

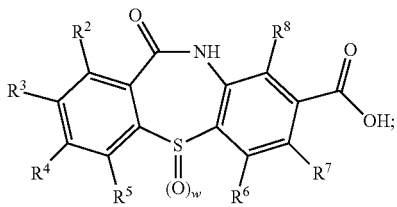

Formula VII wherein w is 0, 1 or 2;
R², R³, R⁴, R⁵, R⁶, R⁷, and R⁸ are each independently selected from the group consisting of hydrogen, halogen, $C_{1-6}$alkyl, and $C_{1-6}$alkoxy; wherein $C_{1-6}$alkyl and $C_{1-6}$alkoxy may be optionally substituted with one, two, three or more substituents each independently selected from the group consisting of halogen, hydroxyl, and $C_{1-6}$alkoxy; to provide the compound of Formula I.

In certain embodiments, amidating the compound of Formula II may comprise, for example, contacting the compound of Formula II with an amine base and an acylating agent. For example, the acylating agent may be, e.g., an acid anhydride or an acid chloride. For example, the acylating agent may be, e.g., trifluoroacetic anhydride. In one embodiment, the amine base may be, for example, triethylamine.

In other embodiments, oxidizing the compound of Formula III may comprise, for example, contacting the compound of Formula III with a chromium-based oxidizing reagent. For example, the chromium-based oxidizing reagent may be, e.g., Jones reagent.

In some embodiments, cyclizing the compound of Formula IV may comprise, for example, contacting the compound of Formula IV with a thionating reagent. For example, the thionating reagent may be, e.g., phosphorus pentasulfide.

In certain embodiments, hydrolyzing the compound of Formula V may comprise, for example, contacting the compound of Formula V with an aqueous amine base. For example, the aqueous amine base may be, e.g., aqueous methylamine.

In further embodiments, coupling the compound of Formula VI with the compound of Formula VII may be conducted, for example, in the presence of a coupling agent. For example, the coupling agent may be, e.g., hydroxybenzotriazole/ethyl-(N',N'-dimethylamino)propylcarbodiimide hydrochloride.

In some embodiments, R², R³, R⁴, R⁵, R⁶, R⁷, and R⁸ may each independently selected, for example, from the group consisting of, e.g., hydrogen, fluoride, chloride, methyl, and methoxy.

In an embodiment, R¹ may be, for example, trifluoromethyl. For example, the compound of Formula VI may be:

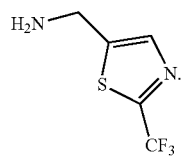

In certain embodiments, the compound of Formula I may be, for example:

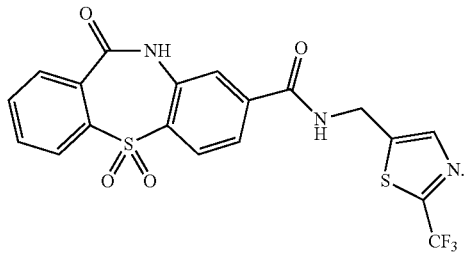 [SMILES: O=C(NCc1cnc(C(F)(F)F)s1)c1ccc2c(c1)NC(=O)c1ccccc1S2(=O)=O]

Also provided herein is a process for preparing a compound represented by Formula VIII:

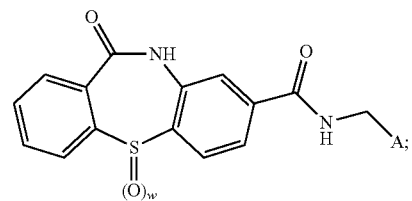

Formula VIII wherein w is 0, 1 or 2;
A is a 5-6 membered heteroaryl having 1, 2 or 3 heteroatoms each independently selected from the group consisting of S, N, and O; wherein said heteroaryl may optionally be substituted with one or more substituents selected from $R^f$;
$R^f$ is independently selected, for each occurrence, from the group consisting of hydrogen, halogen, hydroxyl, cyano, $R^aR^bN$—, $R^aR^bN$-carbonyl-, $R^aR^bN$—$SO_2$—, $C_{1-6}$alkyl, $C_{3-6}$cycloalkyl, $C_{2-6}$alkenyl, $C_{2-6}$alkynyl, $C_{1-6}$alkoxy, $C_{1-6}$alkyl-S(O)$_w$—, (wherein wherein w is 0, 1 or 2), $C_{1-6}$alkylcarbonyl-N($R^a$)— and $C_{1-6}$alkoxycarbonyl-N($R^a$)—; wherein $C_{1-6}$alkyl, $C_{3-6}$cycloalkyl, $C_{2-6}$alkenyl, $C_{2-6}$alkynyl, $C_{1-6}$alkoxy, $C_{1-6}$alkyl-S(O)$_w$—, $C_{1-6}$alkylcarbonyl-N($R^a$)—, $C_{1-6}$alkoxycarbonyl-N($R^a$)— may be optionally substituted by one or more substituents selected from the group consisting of halogen, hydroxyl, and $C_{1-6}$alkoxy;
$R^a$ and $R^b$ are independently selected, for each occurrence, from the group consisting of hydrogen and $C_{1-3}$alkyl; wherein $C_{1-3}$alkyl may optionally be substituted by one or more substituents selected from fluorine, hydroxyl, $C_{1-3}$alkoxy; or $R^a$ and $R^b$, together with the nitrogen to which they are attached, may form a 4-6 membered heterocyclic ring; comprising:
coupling a compound of Formula IX:

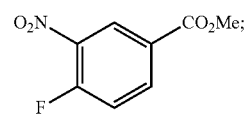

Formula IX with a compound of Formula X:

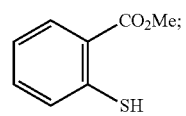

Formula X to provide a compound of Formula XI:

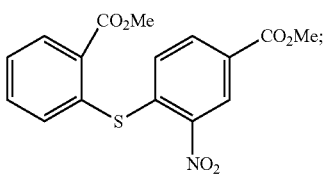

Formula XI optionally oxidizing the compound of Formula XI to provide a compound of Formula XII:

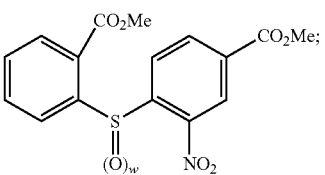

Formula XII wherein w is 1 or 2;
reducing the compound of Formula XII to provide a compound of Formula XIII:

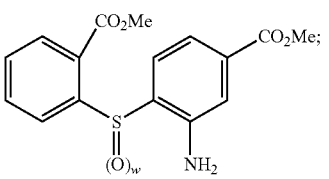

Formula XIII wherein w is 1 or 2;
hydrolyzing the compound of Formula XIII to provide a compound of Formula XIV:

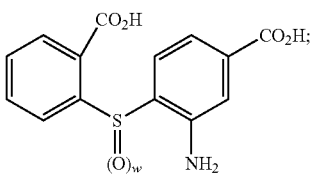

Formula XIV cyclizing the compound of Formula XIV to provide a tricyclic compound of Formula VII:

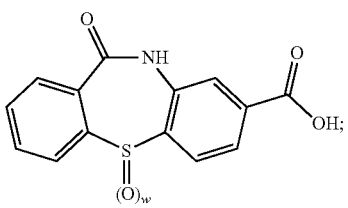

Formula VII and amidating the compound of Formula VII to provide the compound of Formula VIII.

In certain embodiments, coupling the compound of Formula IX with the compound of Formula X may be conducted, for example, in the presence of a base. For example, the base may be, e.g., cesium carbonate.

In some embodiments, oxidizing the compound of Formula XI may comprise, for example, contacting the compound of Formula XI with aqueous hydrogen peroxide. In other embodiments, oxidizing the compound of Formula XI may comprise, for example, contacting the compound of Formula XI with sodium metaperiodate and catalytic ruthenium (III) chloride.

In one embodiment, reducing the compound of Formula XII may comprise, for example, contacting the compound of Formula XII with, e.g., Pd/C under hydrogen gas.

In certain embodiments, hydrolyzing the compound of Formula XIII may comprise, for example, contacting the compound of Formula XIII with an aqueous base. For example, the aqueous base may be, e.g., aqueous lithium hydroxide.

In another embodiment, cyclizing the compound of Formula XIV may comprise, for example, contacting the compound of Formula XIV with, e.g., carbodiimidazole.

In other embodiments, amidating the compound of Formula VII may comprise, for example, contacting the compound of Formula VII with a primary amine represented by A-CH$_2$—NH$_2$ in the presence of a coupling agent. For example, the coupling agent may be, e.g., hydroxybenzotriazole/ethyl-(N',N'-dimethylamino)propylcarbodiimide hydrochloride.

In an embodiment, the primary amine may be represented by, for example:

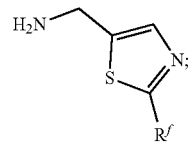

wherein R$^f$ is C$_{1-6}$alkyl optionally substituted by one or more fluorine atoms.

For example, the primary amine may be, e.g.:

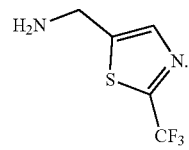

In certain embodiments, the compound of Formula VII may be, for example:

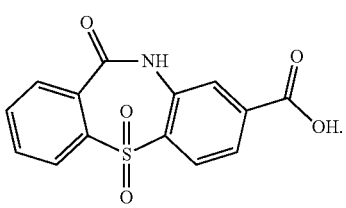

In one embodiment, the compound of Formula VIII may be, for example:

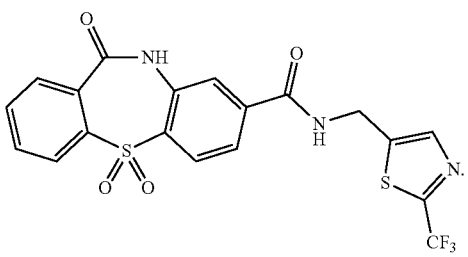 [SMILES: O=C(NCc1cnc(C(F)(F)F)s1)c1ccc2c(c1)NC(=O)c1ccccc1S2(=O)=O]

Also provided herein is a compound or pharmaceutically acceptable salt thereof, represented by:

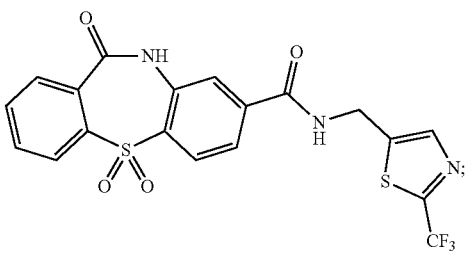 [SMILES: O=C(NCc1cnc(C(F)(F)F)s1)c1ccc2c(c1)NC(=O)c1ccccc1S2(=O)=O]

prepared by the process disclosed herein.

EXAMPLES

The procedures disclosed herein can be conducted in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. At least some of the compounds identified as intermediates e.g., as part of a synthetic scheme disclosed herein, are contemplated as compounds of the invention.

In the procedures described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art (for example, see Greene, Wuts, Protective Groups in Organic Synthesis. 4th Ed. (2007)). The deprotection step may be the final step in the synthesis such that the removal of protecting groups affords compounds of the disclosed process. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

Certain reactions of the disclosed process may be conducted in the presence of a base. Examples of such bases may include, but are not limited to, carbonates such as, e.g., $Li_2CO_3$, $Na_2CO_3$, $K_2CO_3$, $Rb_2CO_3$, $Cs_2CO_3$, $MgCO_3$, $CaCO_3$, $SrCO_3$, $BaCO_3$ and hydrates thereof; and hydroxides such as, e.g., LiOH, NaOH, KOH, $Ca(OH)_2$, $NH_4OH$ and hydrates thereof; and amines such as methylamine, trimethylamine, trimethylamine, diisopropylethylamine, morpholine and morpholine derivatives.

Certain reactions of the disclosed process involving coupling an amino moiety with a carboxylic acid moiety to form an amide may be conducted in the presence of activator(s). Examples of such activators may include, but are not limited to, carbodiimides such as, e.g., N,N'-dicyclohexylcarbodiimide (DCC), N,N'-diisopropylcarbodiimide (DIC), and carbonyl diimidazole (CDI); and triazoles, such as, e.g., 1-hydroxy-benzotriazole (HOBt) and 1-hydroxy-7-aza-benzotriazole (HOAt). Other activators may include, but are not limited to, e.g., HBTU, HATU, HCTU, TBTU, and PyBOP.

Example 1: Synthesis of (2-(trifluoromethyl)thiazol-5-yl)methanamine

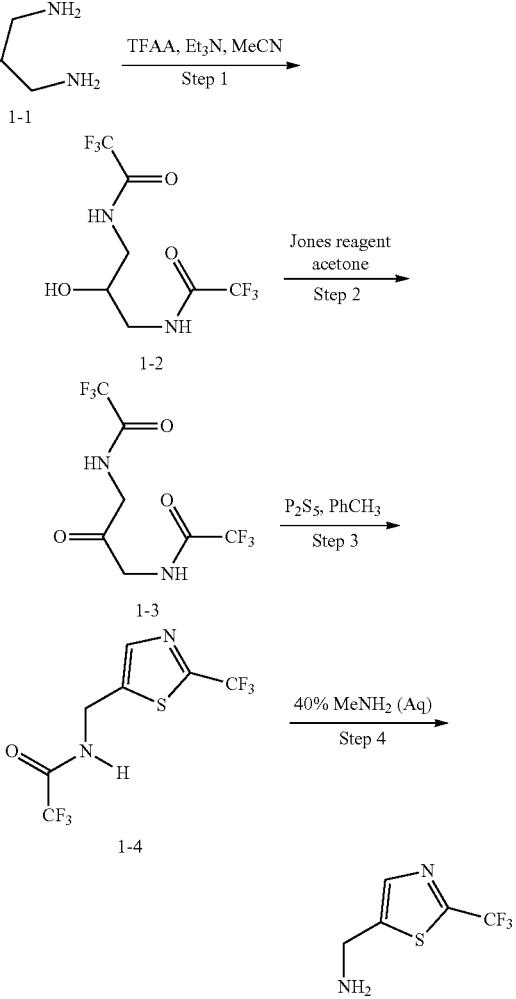

Step 1: Preparation of 1,3-bis trifluoroacetamido-2-propanol (1-2)

The title compound was prepared according to the procedure described in the Supporting Information section of *Org. Lett.* 2008, 10, 2935-2938 as follows. A solution of trifluoroacetic anhydride (7 kg, 4.66 mol) in 15 L of anhydrous acetonitrile was added dropwise to a solution of 1,3-diaminopropan-2-ol (1 kg, 1.11 mol) and triethylamine (3.38 kg; 3.33 mol) in anhydrous acetonitrile (13.3 L) at 0° C. After 2 hours the reaction mixture was warmed to room temperature and stirred for 14 h. The volatiles were removed, the residue dissolved in ethyl acetate (20 L), and washed sequentially with saturated aqueous sodium bicarbonate, saturated ammonium chloride, and brine. The organic layer was dried over anhydrous sodium sulfate, filtered, and concentrated to give a solid. The solids were suspended in petroleum ether (2 L), filtered, and dried to yield 2 kg of the title compound. $^1$H-NMR (DMSO-d6, 300 MHZ): δ 9.43 (d, J=4.8 Hz, 2H), 7.77 (bs, 1H), 3.76 (m, 4H); LCMS-CPI m/z: 283.1 [M+H+].

Step 2: Preparation of 1,3-bis trifluoroacetamido propan-2-one (1-3)

Jones reagent (freshly prepared by dropwise addition of sulfuric acid (1.247 L) to a pre-cooled solution of chromium trioxide (1.347 kg, 13.47 mol) in water (2.695 L)) was added to a stirred solution of bis trifluoroacetamido propan-2-ol (2 kg, 7.09 mol) in acetone (20 L) at 10° C. over 3 h while maintaining the temperature at 10-35° C. The reaction mixture was stirred for an additional 3 h, warmed to room temperature and stirred overnight. The reaction mixture was filtered and the chromium salts washed with acetone (10 L). The combined filtrate was concentrated, washed with petroleum ether and dried to yield 1.49 kg of the title compound which was used without purification in the next step. $^1$H-NMR (DMSO-d6, 300 MHZ): δ 9.74 (t, J=5.4 Hz, 2H), 4.25 (md, J=5.4 Hz, 4H); LCMS-CPI m/z: 281.1 [M+H+].

Step 3: Preparation of 2,2,2-trifluoro-N-((2-(trifluoromethyl)thiazol-5-yl)methyl) ethanethioamide (1-4)

A 20 L round bottom flask was charged with a solution of 1,3-bis trifluoroacetamido propan-2-one (800 g; 2.86 mol) in toluene and equipped with a Dean-Stark apparatus. The solution was heated at reflux for 10 h and cooled to room temperature. Phosphorous pentasulfide (1.9 kg; 8.57 mol) was added, and the reaction mixture was heated at reflux for 12 h. The reaction mixture was cooled to room temperature and filtered. The filter cake was washed with toluene (4 L), and the combined filtrate was concentrated to furnish 800 g of the title compound which was used without purification in the next step. $^1$H-NMR (CDCl$_3$, 300 MHZ): δ 8.32 (bs, 1H), 7.92 (s, 1H), 5.14 (d, J=6.0 Hz, 2H); LCMS-CPI m/z: 295.1 [M+H+].

Step 4: Preparation of (2-(trifluoromethyl)thiazol-5-yl)methanamine (1-5)

Aqueous methylamine (40%, 1.58 L, 20.4 mol) was added to 2,2,2-trifluoro-N-((2-(trifluoromethyl)thiazol-5-yl)methyl) ethanethioamide (600 g. 2.04 mol) in a 2 L autoclave and heated for 14 h at 80° C. The autoclave was cooled to room temperature and allowed to stand open for 2 h. The reaction mixture was extracted with dichloromethane (4×300 ml) and the combined organic layers were dried over anhydrous sodium sulfate, filtered and concentrated to give an oily residue. The residue was distilled under high vacuum at 80° C. to provide 160 g of the title compound. $^1$H NMR (DMSO-d$_6$, 400 MHz): δ 7.92 (s, 1H), 6.80 (br s, 2H), 4.01 (s, 2H).

Example 2: Synthesis of (2-ethylthiazol-5-yl) methanamine hydrochloride (2-7) by an Alternative Route

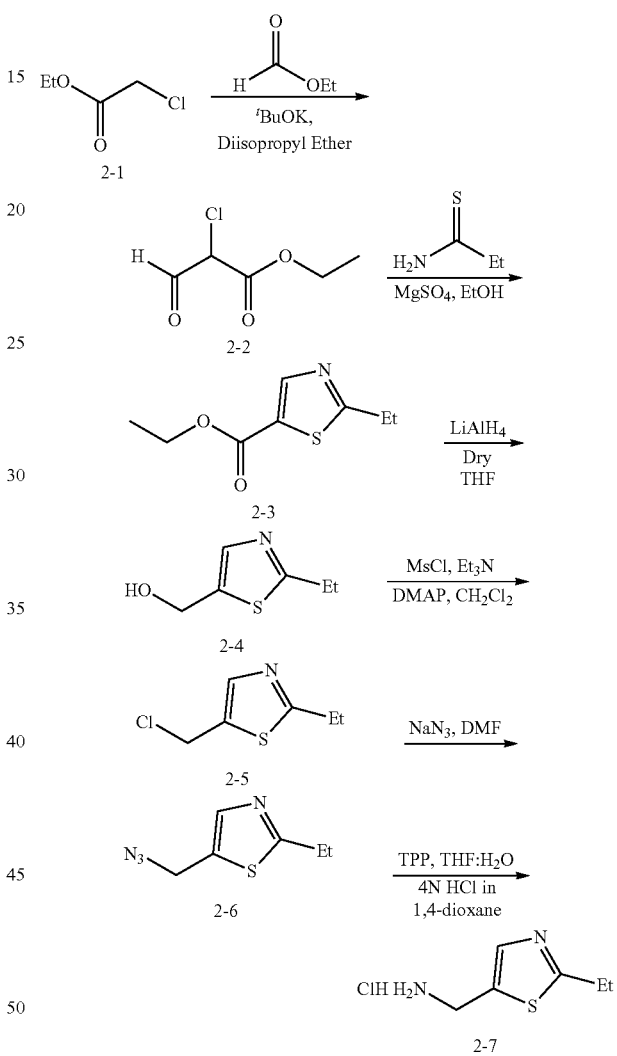

Step 1: Synthesis of ethyl 2-chloro-3-oxopropanoate (2-2)

To a stirring solution of ethyl 2-chloroacetate 2-1 (5 g, 40.98 mmol) and ethyl formate (3.03 g, 40.98 mmol) in diisopropyl ether (100 mL) under argon atmosphere was added potassium tert-butoxide (5.49 g, 45.08 mmol) portion wise for 10 min at 0° C.; warmed to RT and stirred for 24 h. The reaction was monitored by TLC; after completion of the reaction, the pH of the reaction mixture was adjusted to ~6 using 5 N HCl. The obtained solid was filtered, washed with diethyl ether (200 mL) and dried in vacuo to afford compound 2-2 (6 g) as pale brown syrup. TLC: 30%

EtOAc/hexanes (R$_f$: 0.2); LC-MS: 21.49%+75.58%; 149.0 (M$^+$−1); (column; X-Select C-18, (50×3.0 mm, 3.5 μm); RT 0.56 min, 0.77 min. 5 Mm Aq.NH$_4$OAc: ACN 0.8 mL/min).

Step 2: Synthesis of ethyl 2-ethylthiazole-5-carboxylate (2-3)

To a stirring solution of compound 2-2 (1 g) in ethanol (25 mL) under argon atmosphere were added propanethioamide (594 mg, 6.67 mmol), dry magnesium sulfate (4 g) at RT and heated to reflux for 24 h. The reaction was monitored by TLC; after completion of the reaction, the volatiles were removed in vacuo, diluted with EtOAc (2×100 mL). The combined organic extracts were washed with saturated sodium bicarbonate solution (2×100 mL), brine (50 mL), dried over sodium sulfate, filtered and concentrated in vacuo to obtain the crude. The crude was purified through flash column chromatography using 6% EtOAc/hexanes to afford compound 2-3 (330 mg, 27%) as brown syrup. TLC: 10% EtOAc/hexanes (R: 0.4); $^1$H-NMR (DMSO-d$_6$, 400 MHz): δ 8.29 (s, 1H), 4.30 (q, J=7.1 Hz, 2H), 3.04 (q, J=7.5 Hz, 2H), 1.31 (t, J=7.3 Hz, 3H), 1.29 (t, J=7.3 Hz, 3H).

Step 3: Synthesis of (2-ethylthiazol-5-yl) methanol (2-4)

To a stirring suspension of lithium aluminium hydride (205 mg, 5.40 mmol) in dry THF (15 mL) under inert atmosphere was added compound 2-3 (500 mg, 2.70 mmol) at 0° C.; warmed to RT and stirred for 16 h. The reaction was monitored by TLC; after completion of the reaction, the reaction mixture was cooled to 0° C., quenched with 20% aqueous sodium hydroxide solution (3 mL), filtered through celite and washed with EtOAc (3×100 mL). The filtrate was dried over sodium sulfate, filtered and concentrated in vacuo to afford compound 2-4 (310 mg, 80%) as pale yellow solid. TLC: 50% EtOAc/hexanes (R$_f$: 0.4). $^1$H-NMR (CDCl$_3$, 400 MHz): δ 7.51 (s, 1H), 4.82 (s, 2H), 3.01 (q, J=7.5 Hz, 2H), 1.38 (t, J=7.6 Hz, 3H).

Step 4: Synthesis of 5-(chloromethyl)-2-ethylthiazole (2-5)

To a stirring solution of compound 2-4 (300 mg, 2.09 mmol) in CH$_2$Cl$_2$ (15 mL) under inert atmosphere were added triethyl amine (0.6 mL, 4.20 mmol), DMAP (25.6 mg, 0.21 mmol) and methanesulfonyl chloride (0.19 mL, 2.51 mmol) at 0° C.; warmed to RT and stirred for 2 h. The reaction was monitored by TLC; after completion of the reaction, the reaction mixture was diluted with water (50 mL) and extracted with CH$_2$Cl$_2$ (3×100 mL). The combined organic extracts were dried over sodium sulfate, filtered and concentrated in vacuo to afford compound 2-5 (500 mg, crude) as pale yellow syrup. TLC: 30% EtOAc/hexanes (R$_f$: 0.8); LC-MS: 30.71%; 162.0 (M++1); (column; Ascentis Express C18, (50×3.0 mm, 2.7 μm); RT 2.14 min. 0.025% Aq. TFA+5% ACN: ACN+5% 0.025% Aq. TFA, 1.2 mL/min).

Step 5: Synthesis of 5-(azidomethyl)-2-ethylthiazole (2-6)

To a stirring solution of compound 2-5 (500 mg, 2.26 mmol) in DMF (20 mL) under inert atmosphere was added sodium azide (294 mg, 4.52 mmol) at RT and heated to 80° C. for 16 h. The reaction was monitored by TLC; after completion of the reaction, the reaction mixture was diluted with ice cold water (50 mL) and extracted with EtOAc (3×100 mL). The combined organic extracts were dried over sodium sulfate, filtered and concentrated in vacuo to obtain the crude. The crude was purified through flash column chromatography using 15% EtOAc/hexanes to afford compound 2-6 (250 mg, 71%) as pale yellow syrup. TLC: 20% EtOAc/hexanes (R$_f$: 0.4); $^1$H-NMR (CDCl$_3$, 400 MHz): δ 7.56 (s, 1H), 4.49 (s, 2H), 3.03 (q, J=7.6 Hz, 2H), 1.40 (t, J=7.6 Hz, 3H).

Step 6: Synthesis of (2-ethylthiazol-5-yl) methanamine hydrochloride (2-7)

To a stirring solution of compound 2-6 (250 mg, 1.48 mmol) in THF: H$_2$O (5:1, 12 mL) was added triphenyl phosphine (780 mg, 2.97 mmol) at RT and stirred for 2 h. The reaction was monitored by TLC; after completion of the reaction, the volatiles were removed in vacuo to obtain the crude. The obtained solid was further dried using toluene (2×5 mL) to obtain the crude amine. The crude product was dissolved in CH$_2$Cl$_2$ (5 mL) added 4 N HCl in 1,4-dioxane (4 mL) under inert atmosphere at 0° C. and stirred for 30 min. The volatiles were removed in vacuo to obtain the crude, which was triturated with EtOAc (2 mL), diethyl ether (2 mL) and pentane (5 mL) to afford compound 2-7 (180 mg, 68%) as an off-white solid. TLC: 5% MeOH/ CH$_2$Cl$_2$ (R$_f$: 0.2); $^1$H NMR (DMSO-d$_6$, 500 MHz): δ 8.48 (br s, 3H), 7.74 (s, 1H), 4.25 (q, J=5.5 Hz, 2H), 2.98 (q, J=7.5 Hz, 2H), 1.28 (t, J=7.5 Hz, 3H).

Example 3: Synthesis of 11-oxo-10, 11-dihydrodibenzo [b,f] [1, 4] thiazepine-8-carboxylic acid 5, 5-dioxide (3-7)

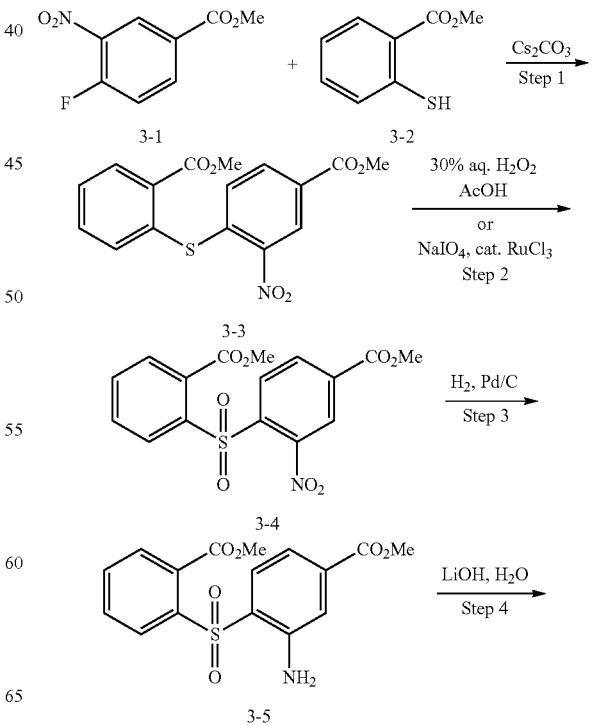

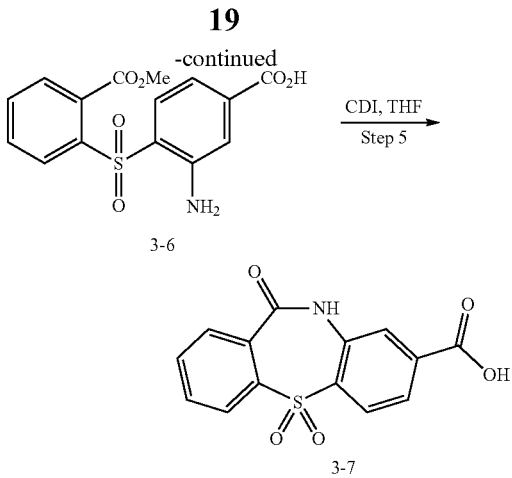

Step 1: Preparation of methyl 4-((2-(methoxycarbonyl) phenyl) thio)-3-nitrobenzoate (3-3)

To a stirred solution of methyl 4-fluoro-3-nitrobenzoate (300 g, 1.0 eq.) and methylthiosalicylate (278.7 g, 1.1 eq.) in DMF (1.8 L) was added $Cs_2CO_3$ (589 g, 1.2 eq.) in batches at 0 to 5° C. The reaction mixture was stirred at 0 to 5° C. for 30 min, warmed to room temperature over 2 h, and stirred at room temperature for 2 h. The reaction mixture was cooled to 10-15° C., diluted with water (26 V) and stirred for 30 min. The solids were collected by filtration, washed with water (20 V) and n-heptane (10 V), and dried under reduced pressure below 50° C. The dry solids were suspended in n-heptane (10 V) at 90-95° C. to form a slurry and cooled to 35-40° C. The solids were collected by filtration, washed with n-heptane (5 V), and dried under reduced pressure for 8 h to yield the title compound 3-3. Yield: (92.96%), Purity: 99.01%. TLC: 20% EtOAc/hexanes ($R_f$: 0.4); $^1$H NMR ($CDCl_3$, 400 MHz): δ 8.85 (s, 1H), 7.99-7.92 (m, 2H), 7.66-7.56 (m, 3H), 6.93 (d, J=8.6 Hz, 1H), 3.94 (s, 3H), 3.79 (s, 3H); LCMS-ESI m/z: 348 [M+H+].

Step 2: Preparation of methyl 4-((2-(methoxycarbonyl)phenyl)sulfonyl)-3-nitrobenzoate (3-4)

Oxidation Method A:
To a stirred solution of methyl 4-((2-(methoxycarbonyl) phenyl) thio)-3-nitrobenzoate (2.3 Kg, 1.0 eq.) in AcOH (23 L, 10 V) at 85° C. was added 30% aqueous $H_2O_2$ (25 L, 10 V). The reaction mixture was stirred at 85° C. for 10 h, and a second portion of 30 aqueous % $H_2O_2$ (23 L, 10 V) was added and stirred at 90° C. for 10 h. A third portion of 30% aqueous $H_2O_2$ (11.5 L, 5 V) was added and stirred for 4 h. The reaction mixture was cooled to ~15° C. and the solids were collected by filtration, washed with water (23 L, 10V) and dried under reduced pressure below 50° C. for 10 h to provide 2.14 kg of the title compound. HPLC analysis indicated a purity of 98.55%, with 0.46% of the mono-oxidized sulfoxide. $^1$H-NMR (DMSO-d6, 500 MHZ): δ 8.51 (s, 1H), 8.39-8.41 (dd, J=1.5, 8.5 HZ, 1H), 8.16-8.18 (dd, J=2.0, 7.5 HZ, 1H), 8.13 (d, J=8.5 HZ, 1H), 7.91-7.94 (m, 2H), 7.86-7.88 (m, 1H), 3.93 (s, 3H), 3.67 (s, 3H); LCMS-ESI m/z: 397 [M+$NH_4$+], m/z: 402 [M+Na+].

Oxidation Method B:
To a stirred solution of methyl 4-((2-(methoxycarbonyl) phenyl) thio)-3-nitrobenzoate (300.0 g, 1.0 eq.) in $CH_2Cl_2$:acetone:$H_2O$ (1.5 L:1.5 L:3.0 L) at room temperature was added sodium metaperiodate (461.0 g, 2.5 eq.) and ruthenium (III) chloride (60 mg, 0.0003 eq.). After 5 h the acetone and $CH_2Cl_2$ were removed by vacuum distillation below 50° C. The reaction mixture was diluted with water (1.5 L, 5 V) and stirred at room temperature for 2-3 h. The reaction mixture was filtered and the filter cake was washed with water (3.0 L, 10 V) and dried under vacuum at 50-55° C. for 12-16 h to yield 315 g of the title compound. HPLC analysis indicated a purity of 99.9%. The structure of the product was confirmed by $^1$H NMR and MS to be identical to that obtained by Method A.

Step 3: Preparation of methyl 3-amino-4-((2-(methoxycarbonyl)phenyl)sulfonyl)benzoate (3-5)

To a stirred solution of methyl 4-((2-(methoxycarbonyl) phenyl)sulfonyl)-3-nitrobenzoate (100.0 g, 1.0 eq.) in EtOAc (2.5 L, 25 V) at room temperature was added 10% Pd/C (50% wet, 26.0 g, 26 wt %). The reaction mixture was stirred under $H_2$ in an autoclave at 10 kg/cm$^2$ for 22 h. The reaction mixture was filtered through celite, and the filter cake washed with 20% MeOH/EtOAc (100 V). The combined filtrate was concentrated to ~2 V, diluted with n-heptane (5 V), and concentrated. A second portion of n-heptane (5 V) was added and the reaction mixture was stirred at room temperature for 2-3 h. The solids were collected by filtration, and dried under reduced pressure below 50° C. for 10 h to yield 80.0 g (87%) of the title compound 3-5. HPLC analysis indicated a purity of 97.75%. $^1$H-NMR (DMSO-d6, 500 MHZ): δ 8.14 (d, J=7.5 HZ, 1H), 7.80 (t, J=7.5 HZ, 1H), 7.72 (d, J=8.0 Hz, 1H), 7.74-7.76 (m, 1H), 7.66 (d, J=7.5 Hz, 1H), 7.46 (d, J=1.5 Hz, 1H), 7.19-7.21 (dd, J=1.5, 8.0 Hz, 1H), 6.38 (s, 2H), 3.83 (s, 3H), 3.83 (s, 3H); LCMS-ESI m/z: 350 [M+H+], m/z: 372 [M+Na+].

Step 4: Preparation of 3-amino-4-((2-carboxyphenyl)sulfonyl)benzoic Acid (3-6)

To a stirred solution of methyl 3-amino-4-((2-methoxycarbonyl)phenyl)sulfonyl) benzoate (1.5 Kg, 1.0 eq.) in THF (20 V) at room temperature was added a solution of LiOH.$H_2O$ (10 eq.) in water (10 V). After stirring at 45° C. for 12 h, the THF was removed by distillation. The reaction mixture was diluted with water (5 V) and extracted with EtOAc (2×6 V). The aqueous layer was cooled to 10° C., acidified with 5 N HCl (8 V) to pH 2, and stirred at 10-15° C. for 2 h. The aqueous layer was filtered, the filter cake washed with water (2×20 V) and heptane (2×5 V), and dried under reduced pressure below 50° C. for 26 h to afford 1.30 kg of a mixture of the title compound (65.02%) and 11-oxo-10,11-dihydrodibenzo[b,f][1,4] thiazepine-8-carboxylic acid 5,5-dioxide (34.70%), which was used without purification in the next step. Characterization of 3-amino-4-((2-carboxyphenyl)sulfonyl)benzoic acid: $^1$H-NMR (DMSO-d6, 500 MHZ): δ 13.6 (bs 2H), 8.07 (d, J=7.5 HZ, 1H), 7.74-7.76 (m, 2H), 7.68 (t, J=7.5 HZ, 1H), 7.62 (d, J=7.5 Hz, 1H), 7.40 (d, J=1.5 Hz, 1H), 7.13-7.15 (dd, J=1.5, 8.0 Hz, 1H), 6.39 (bs, 2H); LCMS-ESI m/z: 322 [M+H+], m/z: 344 [M+Na+].

Step 5: Preparation of 11-oxo-10,11-dihydrodibenzo [b,f][1,4] thiazepine-8-carboxylic Acid 5,5-dioxide (3-7)

To a stirred solution of the crude product mixture of Step 5 (60.0 g, 1.0 eq.) in THF (15 V) at 15-20° C. was added CDI (3.0 eq.). The reaction mixture was warmed to room temperature and stirred for 18 h. The reaction mixture was diluted with water (15 V) and the THF was removed under reduced pressure. The reaction mixture was further diluted with water (2 V) and EtOAc (5 V) and stirred for 15-20 min. The crude suspension was filtered and the filter cake retained. The organic and aqueous layers of the filtrate were separated, and the aqueous layer was acidified with 5 N HCl (6 V) to pH 2 at 15-20° C. to obtain a precipitate. The aqueous layer was filtered, the filter cake washed with water (5 V) and dried under reduced pressure for 2 h. The two filter cakes were combined and stirred in 10% aqueous NaOH (6 V) at 0° C. for 1-2 h to obtain a clear solution. The solution was acidified to pH 2 with 5 N HCl (5-6 V) at 5-10° C. to obtain a precipitate. The precipitate was filtered, the filter cake washed with water (10 V) and dried under reduced pressure at 50-55° C. for 24 h to obtain the title compound. TLC: 5% MeOH/CH$_2$Cl$_2$ (R$_f$: 0.1); $^1$H NMR (DMSO-d$_6$, 400 MHz): δ 13.65 (br s, 1H), 11.55 (s, 1H), 8.07 (d, J=8.3 Hz, 1H), 8.03-7.82 (m, 6H).

3-Step Telescoping Method Combining Steps 3, 4 and 5

To a stirred solution of methyl 4-((2-(methoxycarbonyl) phenyl)sulfonyl)-3-nitrobenzoate (100.0 g, 1.0 eq.) in THF (0.5 L, 5 V) was added 10% Pd—C(50% wet, 10.0 g, 10 wt %) at room temperature. The reaction mixture was stirred under H$_2$ in an autoclave at 10 kg/cm$^2$ pressure for 20 h. HPLC analysis indicated completion of the reaction and a product purity of 98.62%. The reaction mixture was filtered through a celite, the filter cake washed with hot THF (10 V), and the combined filtrate was used directly in the next step.

To the above combined filtrate (~1.7 L) was added water (0.8 L, 10 V) and LiOH.H$_2$O (96.1 g, 10 eq). After stirring at 45-50° C. for 16 to 18 h, the THF layer was separated and the aqueous layer was washed with EtOAc (5 V). The aqueous layer was acidified to pH 2 at room temperature with 5 M HCl (5-6 V), with an observed exotherm of 10-15° C. The aqueous layer was stirred at room temperature for 1-2 h and filtered. The filter cake was washed with water (15 V) and n-heptane (10 V) and dried under vacuum below 50-55° C. for 16-18 h to obtain a crude solid which was used directly in the next step.

To a stirred solution of the above crude material (65.0 g, 1.0 eq.) in THF (15 V) was added CDI (3.0 eq.) at 15-20° C. The reaction mixture was warmed to room temperature over 30 min and stirred for 18 h. The reaction mixture was diluted with water (15 V) and the THF removed under reduced pressure. The reaction mixture was diluted with water (2 V) and EtOAc (5 V), stirred for 15-20 min, filtered, and the filter cake retained. The organic and aqueous layers of the filtrate were separated, and the aqueous layer was acidified with 5 N HCl (6 V) to pH 2 at 15-20° C. to obtain a precipitate. The aqueous layer was filtered, the filter cake washed with water (5 V) and dried under reduced pressure for 2 h.

The two filter cakes were combined and stirred in 10% aqueous NaOH (6 V) at 0° C. for 1-2 h to obtain a clear solution. The solution was acidified to pH 2 with 5 N HCl (5-6 V) at 5-10° C. to obtain a precipitate. The precipitate was filtered, the filter cake washed with water (10 V) and dried under reduced pressure at 50-55° C. for 24 h to obtain 11-oxo-10,11-dihydrodibenzo[b,f][1,4] thiazepine-8-carboxylic acid 5,5-dioxide. $^1$H-NMR (DMSO-d6, 500 MHZ): δ 13.6 (bs 2H), 11.54 (s, 1H), 8.07 (d, J=8.5 HZ, 1H), 7.97-8.01 (m, 2H), 7.94 (s, 1H), 7.84-7.93 (m, 3H), 6.39 (bs, 2H); LCMS-ESI m/z: 302 [M−H$^-$].

Example 4: Synthesis of 11-oxo-N-((2-(trifluoromethyl)thiazol-5-yl)methyl)-10,11-dihydrodibenzo[b,f][1,4]thiazepine-8-carboxamide 5,5-dioxide

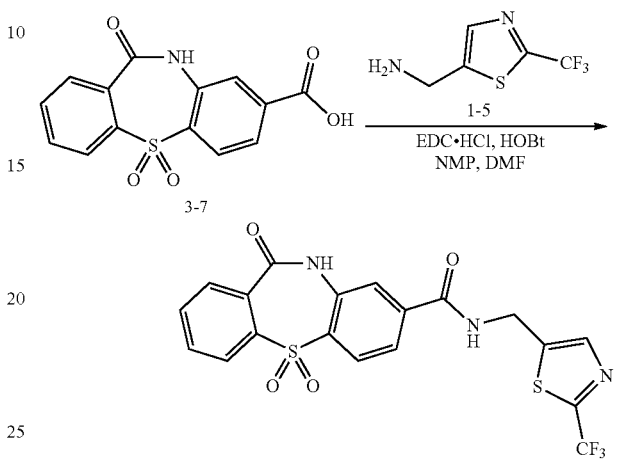

To a stirred solution of 11-oxo-10,11-dihydrodibenzo[b,f][1,4] thiazepine-8-carboxylic acid 5,5-dioxide 3-7 (30.0 g, 1.0 eq.) in DMF (300 mL, 10 V) at 0-5° C. was added N-methyl morpholine (43.5 mL, 4.0 eq.), 2-trifluoromethyl-5-aminomethylthiazole (25.2 g, 1.4 eq.), EDC.HCl (28.4 g, 1.5 eq.) and HOBt (20.2 g, 1.5 eq.) under nitrogen. The reaction mixture was warmed to room temperature and stirred for 16 h. The reaction mixture was diluted with water (30 V) to obtain a suspension which was stirred at room temperature for 2-3 h. The suspension was filtered, the filter cake washed with water (2×10 V), and dried under vacuum for 24 h below 45° C. to obtain a crude solid. To the crude solid was added EtOAc:THF (100:10) V) and activated charcoal (15 wt %). The reaction mixture was stirred at 60-65° C. for 3 h, cooled to 35-40° C. and filtered through celite. The obtained filtrate was concentrated to 3 V, diluted with n-heptane (5 V) stirred at room temperature for 1-2 h, and filtered. The filter cake was washed with n-heptane (5 V) and dried under vacuum below 50° C. for 8-10 h to give the title compound in 75% yield. HPLS analysis indicated a purity of 99.70%. MS (m/z) calcd. for C$_{19}$H$_{12}$F$_3$N$_3$O$_4$S$_2$ ([M+H]$^+$): 467.0; found: 468.3; $^1$H-NMR (DMSO-d$_6$, 400 MHz): δ 11.50 (s, 1H), 9.56 (t, J=5.6 Hz, 1H), 8.08-8.04 (m, 2H), 7.98 (td, J=7.7, 0.9 Hz, 2H), 7.94-7.83 (m, 3H), 7.81 (dd, J=8.2, 1.4 Hz, 1H), 4.75 (d, J=5.5 Hz, 2H).

Example 5: 1-fluoro-11-oxo-10,11-dihydrodibenzo[b,f][1,4]thiazepine-8-carboxylic Acid 5,5,-dioxide (5-7)

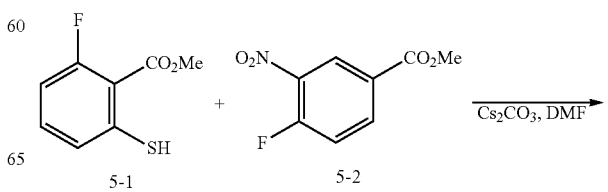

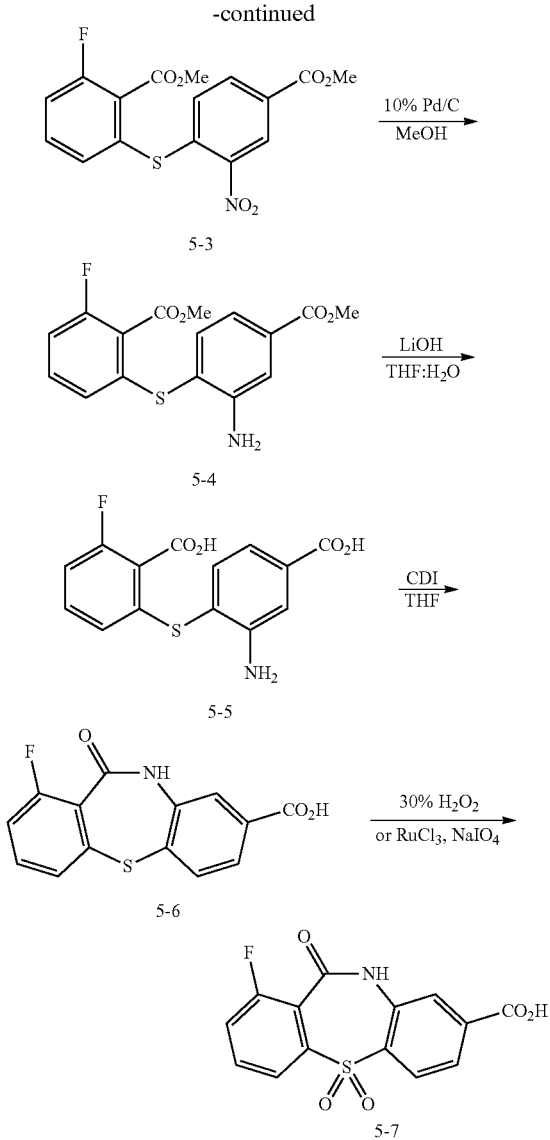

Step 1: Synthesis of methyl 2-fluoro-6-((4-(methoxycarbonyl)-2-nitrophenyl) thio) benzoate To a stirred solution of methyl 4-fluoro-3-nitrobenzoate (4.5 g, 22.61 mmol) in DMF (100 mL) under inert atmosphere were added methyl 2-fluoro-6-mercaptobenzoate (4.6 g, crude), cesium carbonate (11 g, 33.91 mmol) at RT; heated to 60-65° C. and stirred for 2 h. The reaction was monitored by TLC; after completion of the reaction, the reaction mixture was diluted with water (600 mL) and stirred for 1 h. The precipitated solid was filtered, titurated with 10% EtOAc/hexanes (2×20 mL) and dried in vacuo to afford compound 25 (7 g, 85%) as yellow solid. TLC: 20% EtOAc/hexanes ($R_f$: 0.3); $^1$H NMR (DMSO-$d_6$, 400 MHz): δ 8.65 (s, 1H), 8.08 (dd, J=8.6, 1.9 Hz, 1H), 7.79-7.72 (m, 1H), 7.67-7.61 (m, 2H), 7.01 (d, J=8.6 Hz, 1H), 3.88 (s, 3H), 3.72 (s, 3H).

Step 2: Synthesis of methyl 2-((2-amino-4-(methoxycarbonyl) phenyl) thio)-6-fluorobenzoate To a stirred solution of methyl 2-((2-amino-4-(methoxycarbonyl) phenyl) thio)-6-fluorobenzoate (7.09 g, 19.17 mmol) in MeOH (200 mL) under inert atmosphere was added 10% Pd/C (3.5 g) at RT and stirred under hydrogen at 80 psi for 16 h in an autoclave. The reaction was monitored by TLC; after completion of the reaction, the reaction mixture was filtered through celite and washed with 40% MeOH/CH$_2$Cl$_2$ (3×500 mL). The combined organic extracts were dried over sodium sulfate, filtered and concentrated in vacuo to obtain the crude product, which was triturated with 20% EtOAc/hexanes (200 mL) and dried in vacuo to afford methyl 2-((2-amino-4-(methoxycarbonyl) phenyl)thio)-6-fluorobenzoate (5 g, 78%) as an off-white solid. TLC: 20% EtOAc/hexanes ($R_f$: 0.4); $^1$H NMR (DMSO-$d_6$, 400 MHz): δ 7.45-7.36 (m, 3H), 7.19-7.11 (m, 2H), 6.68 (d, J=7.7 Hz, 1H), 5.71 (s, 2H), 3.90 (s, 3H), 3.83 (s, 3H).

Step 3: Synthesis of 2-((2-amino-4-carboxyphenyl) thio)-6-fluorobenzoic Acid

To a stirred solution of methyl 2-((2-amino-4-(methoxycarbonyl) phenyl)thio)-6-fluorobenzoate (5 g, 14.92 mmol) in THF: H$_2$O (5:1, 90 mL) was added lithium hydroxide monohydrate (3.13 g, 74.62 mmol) at RT and stirred for 16 h and heated to 80° C. for 5 h. The reaction was monitored by TLC; after completion of the reaction, the volatiles were removed in vacuo. The residue was diluted with water (200 mL) and acidified with 2 N HCl to pH-4. The precipitated solid was filtered and dried in vacuo to afford 2-((2-amino-4-carboxyphenyl) thio)-6-fluorobenzoic acid (4 g, 87%) as an off-white solid. TLC: 30% EtOAc/hexanes ($R_f$: 0.1); $^1$H NMR (DMSO-$d_6$, 400 MHz): δ 12.89 (br s, 1H), 7.42-7.36 (m, 2H), 7.35-7.31 (m, 1H), 7.14-7.08 (m, 2H), 6.63 (d, J=8.0 Hz, 1H), 5.75 (br s, 2H).

Step 4: Synthesis of 1-fluoro-11-oxo-10, 11-dihydrodibenzo [b,f] [1, 4] thiazepine-8-carboxylic Acid (5-6)

To a stirred solution of 2-((2-amino-4-carboxyphenyl) thio)-6-fluorobenzoic acid (4 g, 13.02 mmol) in THF (100 mL) under inert atmosphere was added CDI (10.56 g, 65.1 mmol) at RT and stirred for 26 h. The reaction was monitored by TLC; after completion of the reaction, the volatiles were removed in vacuo. The residue was diluted with ice cold water (80 mL) and acidified with 2 N HCl to pH-4. The precipitated solid was filtered and dried in vacuo to afford 1-fluoro-11-oxo-10, 11-dihydrodibenzo [b, f] [1, 4] thiazepine-8-carboxylic acid (3.3 g, 88%) as an off-white solid. TLC: 15% MeOH/CH$_2$Cl$_2$ ($R_f$: 0.2); $^1$H NMR (DMSO-$d_6$, 400 MHz): δ 13.33 (br s, 2H), 11.00 (s, 1H), 7.77 (s, 1H), 7.69-7.67 (m, 2H), 7.53-7.47 (m, 1H), 7.42-7.39 (m, 1H), 7.35-7.29 (m, 1H).

Step 6: 1-fluoro-11-oxo-10,11-dihydrodibenzo[b,f][1,4]thiazepine-8-carboxylic Acid 5,5-dioxide (5-7)

Treating a sample of 1-fluoro-11-oxo-10, 11-dihydrodibenzo [b,f] [1, 4]thiazepine-8-carboxylic acid under similar oxidative conditions (Method A and Method B) detailed in Example 3, the title compound was obtained.

Example 6: 11-oxo-N-((2-(trifluoromethyl)thiazol-5-yl)methyl)-10,11-dihydrodibenzo[b,f][1,4]thiazepine-8-carboxamide 5,5-dioxide via 11-oxo-N-((2-(trifluoromethyl)thiazol-5-yl)methyl)-10,11-dihydrodibenzo[b,f][1,4]thiazepine-8-carboxamide (6-2)

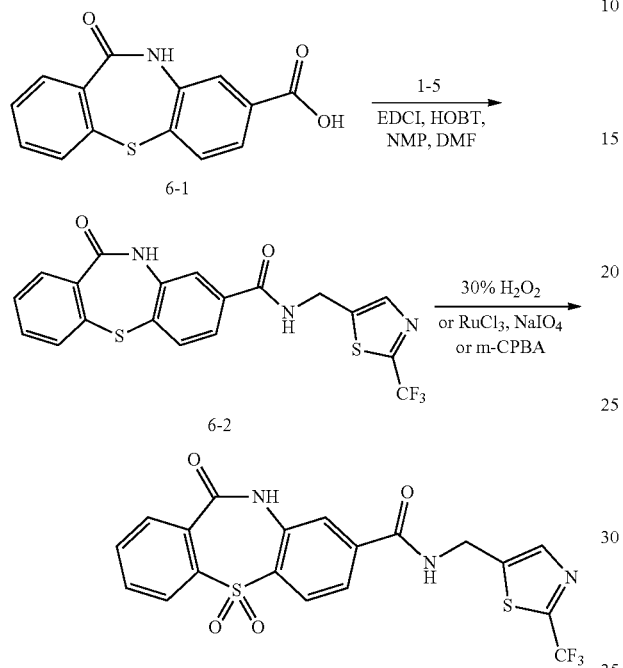

Example 7: Synthesis of 9-chloro-11-oxo-10,11-dihydrodibenzo[b,f][1,4]thiazepine-8-carboxylic Acid 5,5-dioxide (7-9)

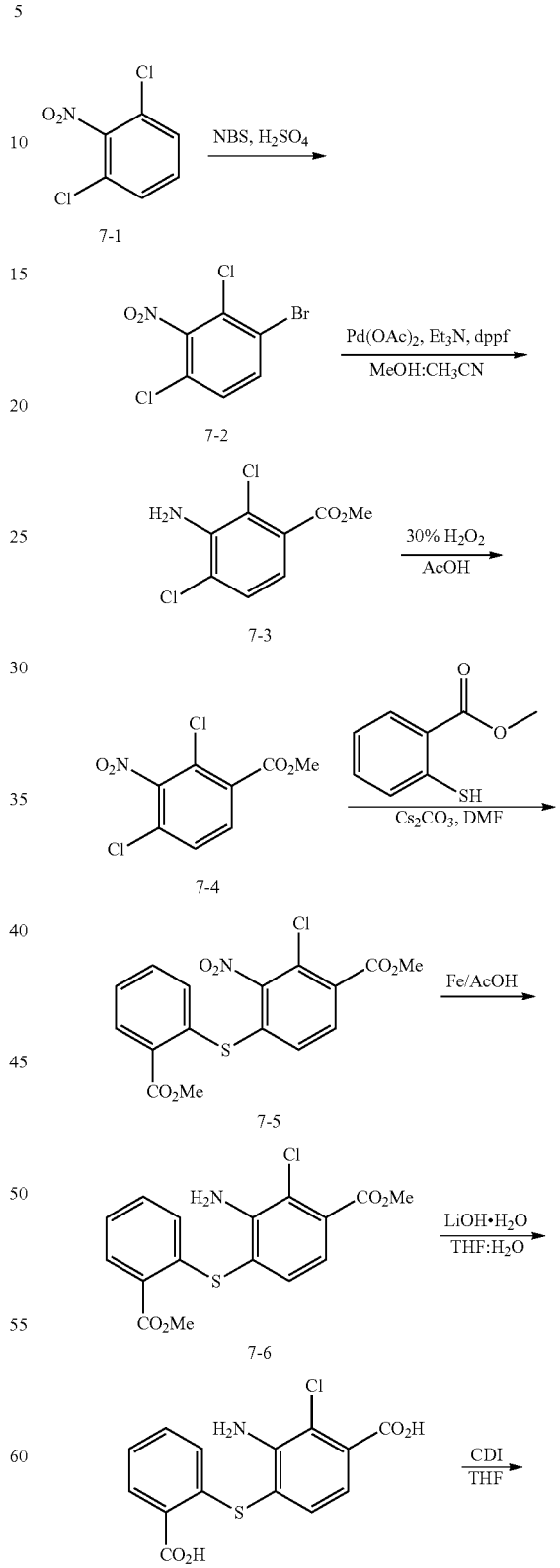

Step 1: Synthesis of 11-oxo-N-((2-(trifluoromethyl)thiazol-5-yl)methyl)-10,11-dihydrodibenzo[b,f][1,4]thiazepine-8-carboxamide (6-2)

The tricyclic thioether carboxylic acid 6-1 was obtained following procedures descried in Example 3 and Example 6.

Following the experimental procedure descried in Example 4 and substituting tricyclic core acid 3-7 with 6-1, the amide 6-2 was obtained. 1H-NMR (DMSO-d6, 400 MHz): δ 10.77 (s, 1H), 9.38 (t, J=5.7 Hz, 1H), 8.05 (s, 1H), 7.72-7.66 (m, 3H), 7.60 (dd, J=8.0, 1.8 Hz, 1H), 7.53 (td, J=7.1, 1.6 Hz, 1H), 7.50-7.43 (m, 2H), 4.72 (d, J=5.6 Hz, 2H); LCMS: m/z: 435.9 [M+H$^+$].

Step 2: 11-oxo-N-((2-(trifluoromethyl)thiazol-5-yl)methyl)-10,11-dihydrodibenzo[b,f][1,4]thiazepine-8-carboxamide 5,5-dioxide The conversion of sulfide functional group in compound 6-2 to the corresponding sulfone compound was achieved by using oxidative conditions as detailed in Method A or Method B of Example 3.

-continued

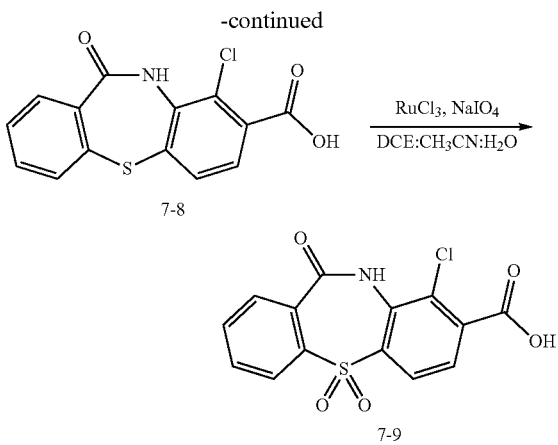

Step 1: Synthesis of 1-bromo-2, 4-dichloro-3-nitrobenzene (7-2)

To a stirring solution of 1,3-dichloro-2-nitrobenzene 7-1 (5 g, 26.04 mmol) in concentrated sulfuric acid (150 mL) under inert atmosphere was added N-bromosuccinimide (4.6 g, 26.04 mmol) portion wise at RT and heated to 60° C. and stirred for 16 h. The reaction was poured into ice-cold water (100 mL) and extracted with EtOAc (2×100 mL). The combined organic extracts were dried over sodium sulfate, filtered and concentrated in vacuo to obtain the crude. The crude was purified through silica gel column chromatography using 2% EtOAc/hexanes to afford compound 128 (4.9 g, 70%). TLC: 5% EtOAc/hexanes ($R_f$: 0.5); $^1$H NMR (DMSO-$d_6$, 400 MHz): δ 8.11 (d, J=8.8 Hz, 1H), 7.79 (d, J=8.9 Hz, 1H).

Step 2: Synthesis of methyl 3-amino-2, 4-dichlorobenzoate (7-3)

To a stirring solution of compound 7-2 (7.5 g, 27.77 mmol) in MeOH: CH$_3$CN (4:1, 100 mL) under inert atmosphere in a steel bomb were added triethylamine (12 mL, 83.33 mmol), dppf (1.53 g, 2.76 mmol), Pd(OAc)$_2$ (500 mg, 2.27 mmol) at RT; heated to 100° C., under CO gas atmosphere (150 psi) and stirred for 16 h. The reaction was monitored by TLC; after completion of the reaction, the reaction mixture was filtered through celite and the filtrate was concentrated in vacuo to obtain the crude. The crude was purified through silica gel column flash chromatography using 15% EtOAc/hexanes to afford compound 7-3 (5 g, 82%). TLC: 30% EtOAc/hexanes ($R_f$: 0.5); $^1$H NMR (DMSO-$d_6$, 400 MHz): δ 7.34 (d, J=8.1 Hz, 1H), 6.94 (d, J=8.1 Hz, 1H), 5.79 (s, 2H), 3.83 (s, 3H).

Step 3: Synthesis of methyl 2, 4-dichloro-3-nitrobenzoate (7-4)

To a stirring solution of compound 7-3 (5 g, 22.72 mmol) in glacial acetic acid (25 mL) was added 30% H$_2$O$_2$ (25 mL) at 0° C.; warmed to RT and stirred for 16 h. The reaction was monitored by TLC; after completion of the reaction, the reaction mixture was diluted with water (100 mL) and EtOAc (200 mL). The organic extract was dried over sodium sulfate, filtered and concentrated in vacuo to afford compound 7-4 (4.1 g, 73%) as brown solid. TLC: 30% EtOAc/hexanes ($R_f$: 0.3); $^1$H NMR (DMSO-$d_6$, 400 MHz): δ 8.11 (d, J=8.5 Hz, 1H), 7.96 (d, J=8.7 Hz, 1H), 3.91 (s, 3H).

Step 4: Synthesis of methyl 2-chloro-4-((2-(methoxycarbonyl) phenyl) thio)-3-nitrobenzoate (7-5)

To a stirring solution of compound 7-4 (4.1 g, 16.40 mmol) in DMF (100 mL) under argon atmosphere were added methyl 2-mercaptobenzoate (2.75 g, 16.40 mmol), cesium carbonate (16 g, 49.23 mmol) at 0° C.; warmed to RT and stirred for 16 h. The reaction was monitored by TLC; after completion of the reaction, the reaction mixture was diluted with water (500 mL) and extracted with EtOAc (200 mL). The organic extract was dried over sodium sulfate, filtered and concentrated in vacuo to compound 7-5 (1 g, 16%) as white solid. TLC: 30% EtOAc/hexanes ($R_f$: 0.3). $^1$H NMR (DMSO-$d_6$, 400 MHz): δ 8.08 (d, J=8.3 Hz, 1H), 7.98 (dd, J=7.8, 1.5 Hz, 1H), 7.73 (d, J=8.3 Hz, 1H), 7.58-7.52 (m, 1H), 7.43 (td, J=7.6, 1.1 Hz, 1H), 7.02 (dd, J=8.0, 0.6 Hz, 1H), 3.92 (s, 3H), 3.86 (s, 3H).

Step 5: Synthesis of methyl 3-amino-2-chloro-4-((2-(methoxycarbonyl) phenyl) thio) benzoate (7-6)

To a stirring solution of compound 7-5 (1 g, 2.62 mmol) in acetic acid (10 mL) was added iron powder (734 mg, 13.12 mmol) at RT; heated to 60° C. and stirred for 4 h. The reaction was monitored by TLC; after completion of the reaction, the volatiles were removed in vacuo and the residue was diluted with EtOAc (200 mL). The organic layer was washed with saturated sodium bicarbonate solution (100 mL) and dried over sodium sulfate, filtered and concentrated in vacuo to afford compound 7-6 (700 mg, 76%) as brown syrup. TLC: 40% EtOAc/hexanes ($R_f$: 0.7). $^1$H NMR (DMSO-$d_6$, 500 MHz): δ 7.97 (br d, J=7.5 Hz, 1H), 7.47-7.42 (m, 2H), 7.26 (br t, J=7.5 Hz, 1H), 6.97 (d, J=8.1 Hz, 1H), 6.65 (br d, J=8.1 Hz, 1H), 5.76-5.73 (m, 2H), 3.89 (s, 3H), 3.87 (s, 3H); LC-MS: 90.61%; 351.8 (M++1); (column; Ascentis Express C18, (50×3.0 mm, 2.7 μm); RT 2.82 min. 0.025% Aq. TFA+5% ACN: ACN+5% 0.025% Aq. TFA, 1.2 mL/min).

Step 6: Synthesis of 3-amino-4-((2-carboxyphenyl) thio)-2-chlorobenzoic Acid (7-7)

To a stirring solution of compound 7-6 (700 mg, 1.99 mmol) in THF:H$_2$O (1:1, 20 mL) was added lithium hydroxide monohydrate (837 mg, 19.94 mmol) portion wise for 10 min at RT and stirred for 16 h. The reaction was monitored by TLC; after completion of the reaction, the volatiles were removed in vacuo. The pH of the residue was adjusted to ~2 with 1 N HCl and extracted with EtOAc (2×50 mL) The organic layer was dried over sodium sulfate, filtered and concentrated in vacuo to compound 7-7 (500 mg, 78%) as a white solid. TLC: 40% EtOAc/hexanes ($R_f$: 0.2). $^1$H NMR (DMSO-$d_6$, 400 MHz): δ 13.29 (br s, 2H), 7.97 (dd, J=7.8, 1.4 Hz, 1H), 7.44-7.38 (m, 2H), 7.26-7.21 (m, 1H), 6.95 (d, J=7.9 Hz, 1H), 6.63 (d, J=7.6 Hz, 1H), 5.62 (br s, 2H); LC-MS: 94.65%; 323.9 (M++1); (column; Ascentis Express C18, (50×3.0 mm, 2.7 μm); RT 1.98 min. 0.025% Aq. TFA+5% ACN: ACN+5% 0.025% Aq. TFA, 1.2 mL/min).

Step 7: Synthesis of 9-chloro-11-oxo-10, 11-dihydrodibenzo [b, f] [1, 4] thiazepine-8-carboxylic Acid (7-8)

To a stirring solution of compound 7-7 (500 mg, 1.42 mmol) in THF (10 mL) under inert atmosphere was added CDI (2.30 g, 14.20 mmol) at RT and stirred for 16 h. The reaction was monitored by TLC; after completion of the reaction, the volatiles were removed in vacuo. The pH of the residue was adjusted to ~2 using 1 N HCl. The precipitated solid was filtered, washed with hexane (20 mL) and dried in vacuo to afford compound 7-8 (300 mg, 69%) as an off-white solid. TLC: 10% MeOH/CH$_2$Cl$_2$ (R$_f$: 0.4); $^1$H NMR (DMSO-d$_6$, 400 MHz): δ 13.62 (br s, 1H), 10.41 (s, 1H), 7.72-7.63 (m, 2H), 7.58-7.54 (m, 1H), 7.53-7.46 (m, 3H); LC-MS: 93.51%; 305.9 (M++1); (column; Ascentis Express C18, (50×3.0 mm, 2.7 m); RT 2.02 min. 0.025% Aq. TFA+5% ACN: ACN+5% 0.025% Aq. TFA, 1.2 mL/min).

Step 8: Synthesis of 9-chloro-11-oxo-10, 11-dihydrodibenzo [b, f] [1, 4] thiazepine-8-carboxylic Acid 5, 5-dioxide (7-9)

To a stirring solution of compound 7-8 (290 mg, 0.95 mmol) in 1, 2 dichloro ethane:CH$_3$CN:H$_2$O (1:1:2, 20 mL) were added sodium metaperiodate (622 mg, 2.85 mmol), ruthenium chloride (10.70 mg, 0.047 mmol) at RT and stirred for 16 h. The reaction was monitored by TLC; after completion, the volatiles were removed in vacuo and the residue was extracted with EtOAc (2×75 mL). The combined organic extracts were dried over sodium sulfate, filtered and concentrated in vacuo to obtain the crude. The crude was purified through silica gel column chromatography using 10% MeOH/CH$_2$Cl$_2$ to afford compound 7-9 (230 mg, 72%) as brown solid. TLC: 40% MeOH/CH$_2$Cl$_2$ (R$_f$: 0.3); $^1$H NMR (DMSO-d$_6$, 400 MHz): δ 14.08 (br s, 1H), 11.13 (s, 1H), 8.01 (d, J=8.2 Hz, 1H), 7.98-7.89 (m, 3H), 7.85 (dd, J=7.5, 1.4 Hz, 1H), 7.71 (d, J=8.2 Hz, 1H); LC-MS: 99.61%; 335.9 (M−1)$^+$; (column; Kinetex EVO C-18 (50×3.0 mm, 2.6 um); RT 1.15 min. 2.5 mM Aq. NH$_4$OOCH+5% ACN: ACN+5% 2.5 mM Aq.NH$_4$OOCH, 0.8 mL/min).

Example 8: Synthesis 9-methyl-11-oxo-10, 11-dihydrodibenzo [b, f] [1, 4] thiazepine-8-carboxylic Acid 5, 5-dioxide (8-9): A Common Intermediate

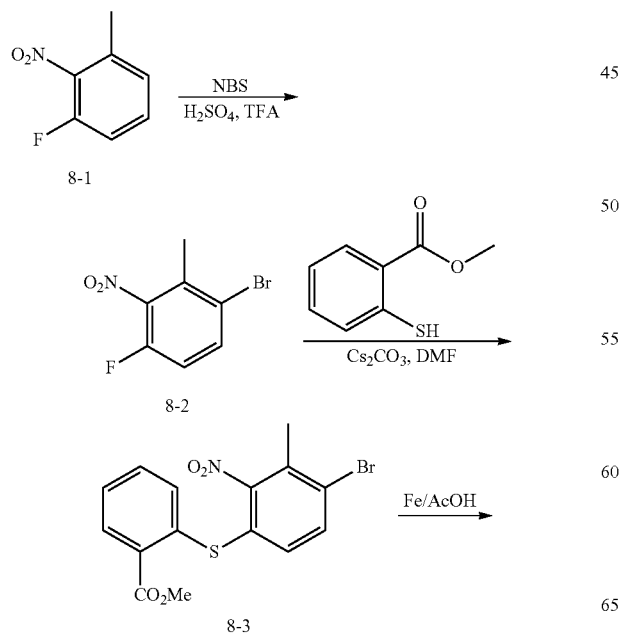

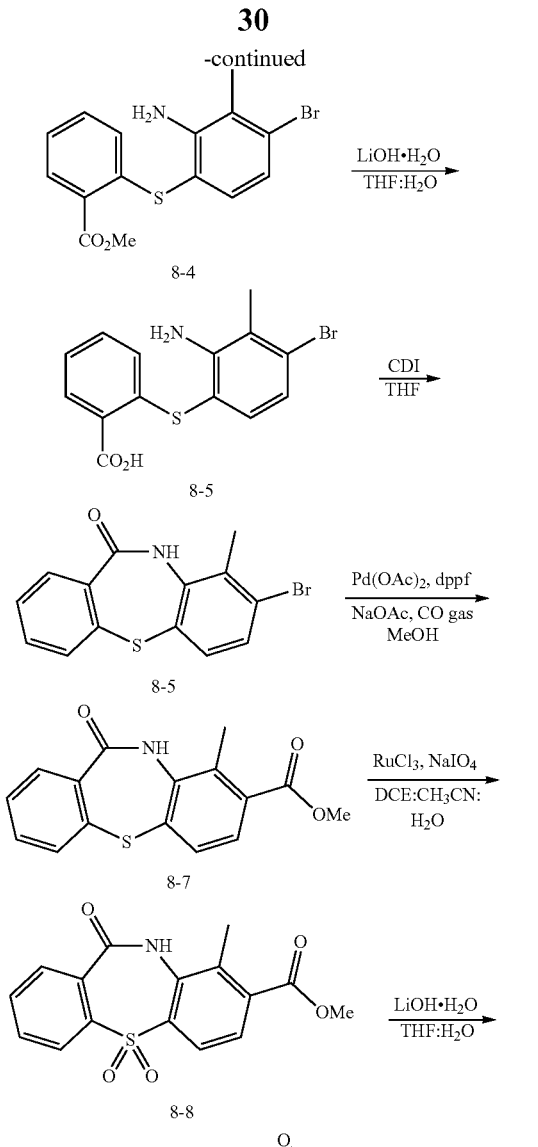

Step 1: Synthesis of 1-bromo-4-fluoro-2-methyl-3-nitrobenzene (8-2)

To 1-fluoro-3-methyl-2-nitrobenzene 8-1 (5 g, 32.25 mmol) at 0° C. under argon atmosphere was added concentrated sulfuric acid:trifluoroacetic acid (1:2, 45 mL). To this was added N-bromosuccinimide (8.61 g, 48.37 mmol) portion wise for 15 min; warmed to RT and stirred for 5 h. The reaction was monitored by TLC; after completion of the reaction, the reaction mixture was poured into ice-cold water (200 mL), the precipitated solid was filtered, washed with water (100 mL) and dried in vacuo to afford the crude. The crude was purified through silica gel flash column chromatography using 1-2% EtOAc/hexanes to afford compound 8-2 (5.1 g, 68%). TLC: 5% EtOAc/hexanes (R$_f$: 0.8); TLC:

30% EtOAc/hexanes (R$_f$: 0.3). $^1$H NMR (DMSO-d$_6$, 400 MHz): δ 7.96 (dd, J=8.9, 5.2 Hz, 1H), 7.47 (t, J=9.2 Hz, 1H), 22.35 (m, 3H);

Step 2: Synthesis of methyl 2-((4-bromo-3-methyl-2-nitrophenyl) thio) benzoate (8-3)

To a stirring solution of compound 8-2 (5.1 g, 21.79 mmol) in DMF (80 mL) under argon atmosphere were added cesium carbonate (10.62 g, 32.67 mmol), methyl 2-mercaptobenzoate 1 (4.03 g, 23.97 mmol) at RT and stirred for 2 h. The reaction was monitored by TLC; after completion of the reaction, the reaction mixture was diluted with ice-cold water (100 mL), the precipitated solid was filtered, washed with hexane (100 mL) and diethyl ether (100 mL) and dried in vacuo to afford compound 8-3 (7.0 g, 84%) as an off-white solid. TLC: 10% EtOAc/hexanes (R$_f$: 0.3); $^1$H NMR (DMSO-d$_6$, 400 MHz): δ 8.09-7.85 (m, 2H), 7.55-7.46 (m, 2H), 7.34 (td, J=7.6, 1.1 Hz, 1H), 6.81 (dd, J=8.2, 0.8 Hz, 1H), 3.87 (s, 3H), 2.35 (s, 3H); LC-MS: 98.98%; 383.2 (M+2)+; (Column; X-select CSH C-18 (50×3.0 mm, 2.5 um); RT 4.99 min. 2.5 mM Aq. NH$_4$OAc:ACN, 0.8 mL/min).

Step 3: Synthesis of methyl 2-((2-amino-4-bromo-3-methylphenyl) thio) benzoate (8-4)

To a stirring solution of compound 8-3 (7 g, 18.32 mmol) in acetic acid (100 mL) was added iron powder (10.2 g, 182.7 mmol) at RT; heated to 80° C. and stirred for 16 h. The reaction was monitored by TLC and LC-MS; after completion of the reaction, the reaction mixture was filtered through celite, the filtrate was concentrated in vacuo. The residue was diluted with EtOAc (200 mL), washed with water (2×100 mL). The organic extract was dried over sodium sulfate, filtered and concentrated in vacuo to compound 8-4 (5.8 g, 90%) as an off-white solid. TLC: 10% EtOAc/hexanes (R$_f$: 0.2); LC-MS: 98.31%; 353.9 (M++2); (column; Ascentis Express C18, (50×3.0 mm, 2.7 μm); RT 3.06 min. 0.025% Aq. TFA+5% ACN: ACN+5% 0.025% Aq. TFA, 1.2 mL/min).

Step 4: Synthesis of 2-((2-amino-4-bromo-3-methylphenyl) thio) benzoic Acid (8-5)

To a stirring solution of compound 8-4 (4.8 g, 13.63 mmol) in THF:H$_2$O (3:1, 120 mL) was added lithium hydroxide monohydrate (1.72 g, 40.95 mmol) at RT and stirred for 16 h. The reaction was monitored by TLC; after completion, the volatiles were removed in vacuo. The residue was diluted with water (20 mL) and acidified with 2 N HCl to pH ~4-5. The obtained solid was filtered, washed with (50 mL) and dried in vacuo to obtain compound 8-5 (4 g, 87%) as an off-white solid. TLC: 20% EtOAc/hexanes (R$_f$: 0.2); LC-MS: 98.82%; 339.9 (M++2); (column; Ascentis Express C18, (50×3.0 mm, 2.7 μm); RT 2.67 min. 0.025% Aq. TFA+5% ACN: ACN+5% 0.025% Aq. TFA, 1.2 mL/min).

Step 5: Synthesis of 8-bromo-9-methyldibenzo [b,f] [1, 4] thiazepin-11(10H)-one (8-6)

To a stirring solution of compound 8-5 (4.7 g, 13.90 mmol) in THF (100 mL) under inert atmosphere was added CDI (13.50 g, 83.32 mmol) at RT and stirred for 24 h. The reaction was monitored by TLC; after completion of the reaction, the volatiles were removed in vacuo. The pH of the residue was adjusted to ~2 using 2 N HCl. The precipitated solid was filtered, washed with water (50 mL) and dried in vacuo to afford compound 8-6 (3 g, 68%) as white solid. TLC: 30% EtOAc/hexanes (R$_f$: 0.4) $^1$H NMR (DMSO-d$_6$, 400 MHz): δ 10.36 (s, 1H), 7.68-7.63 (m, 1H), 7.54-7.49 (m, 1H), 7.49-7.36 (m, 4H), 2.41 (s, 3H);

Step 6: Synthesis of methyl 9-methyl-11-oxo-10, 11-dihydrodibenzo [b, f] [1, 4]thiazepine-8-carboxylate (8-7)

To a stirring solution of compound 8-6 (1.5 g, 4.68 mmol) in MeOH (30 mL) in a steel bomb under inert atmosphere were added dppf (259 mg, 0.46 mmol), sodium acetate (1.15 g, 14.02 mmol), Pd(OAc)$_2$ (105 mg, 0.46 mmol) at RT and heated to 100° C. under CO gas atmosphere (150 psi) and stirred for 24 h. The reaction was monitored by TLC; after completion of the reaction, the reaction mixture was filtered through celite. The filtrate was concentrated in vacuo to obtain the crude. The crude was purified through silica gel column flash chromatography using 10-20% EtOAc/ hexanes to afford compound 8-7 (1.1 g, 79%). TLC: 20% EtOAc/hexanes (R$_f$: 0.2); LC-MS: 98.18%; 299.9 (M+1)+; (column; Ascentis Express C18, (50×3.0 mm, 2.7 μm); RT 2.38 min. 0.025% Aq. TFA+5% ACN: ACN+5% 0.025% Aq. TFA, 1.2 mL/min).

Step 7: Synthesis of methyl 9-methyl-11-oxo-10, 11-dihydrodibenzo [b, f] [1, 4]thiazepine-8-carboxylate 5, 5-dioxide (8-8)

To a compound 8-7 (1.1 g, 3.67 mmol) in 1, 2 dichloro ethane:CH$_3$CN:H$_2$O (1:1:2, 40 mL) were added sodium metaperiodate (2.35 g, 11.03 mmol), ruthenium chloride (38 mg, 0.18 mmol) at RT and stirred for 16 h. The reaction was monitored by TLC; after completion, the reaction mixture was diluted with ice-cold water (50 mL) and extracted with EtOAc (2×75 mL). The combined organic extracts were dried over sodium sulfate, filtered and concentrated in vacuo to afford compound 8-8 (1 g, 83%) as an white solid. TLC: 40% EtOAc/hexanes (R$_f$: 0.2); $^1$H NMR (DMSO-d$_6$, 400 MHz): δ 10.87 (s, 1H), 7.95-7.84 (m, 4H), 7.83-7.78 (m, 1H), 7.68 (d, J=8.3 Hz, 1H), 3.85 (s, 3H), 2.45 (s, 3H); LC-MS: 98.10%; 332.0 (M+1)+; (column; Ascentis Express C18, (50×3.0 mm, 2.7 μm); RT 2.16 min. 0.025% Aq. TFA+5% ACN: ACN+5% 0.025% Aq. TFA, 1.2 mL/min).

Step 8: Synthesis of 9-methyl-11-oxo-10, 11-dihydrodibenzo [b, f] [1, 4] thiazepine-8-carboxylic Acid 5, 5-dioxide (8-9)

To a stirring solution of compound 8-8 (1.07 g, 3.23 mmol) in THF:H$_2$O (3:1, 18 mL) was added lithium hydroxide monohydrate (407 mg, 9.69 mmol) at 0° C.; warmed to RT and stirred for 16 h. The reaction was monitored by TLC; after completion, the volatiles were removed in vacuo. The pH of the residue was acidified with 2 N HCl to ~2. The precipitated solid was filtered, washed with water (50 mL), hexane (20 mL) and dried in vacuo to afford 8-9 (950 mg, 93%) as white solid. TLC: 5% MeOH/CH$_2$Cl$_2$ (R$_f$: 0.1); $^1$H NMR (DMSO-d$_6$, 400 MHz): δ 3.63 (br s, 1H), 10.85 (s, 1H), 7.96-7.84 (m, 4H), 7.83-7.78 (m, 1H), 7.67 (d, J=8.1 Hz, 1H), 2.48 (s, 3H); LC-MS: 98.67%; 317.9 (M+1)$^+$; (column; Ascentis Express C18, (50×3.0 mm, 2.7 μm); RT 1.81 min. 0.025% Aq. TFA+5% ACN: ACN+5% 0.025% Aq. TFA, 1.2 mL/min).

Example 9: 9-methyl-11-oxo-N-((2-(trifluoromethyl)thiazol-5-yl)methyl)-10,11-dihydrodibenzo[b,f][1,4]thiazepine-8-carboxamide 5,5-dioxide (9-2)

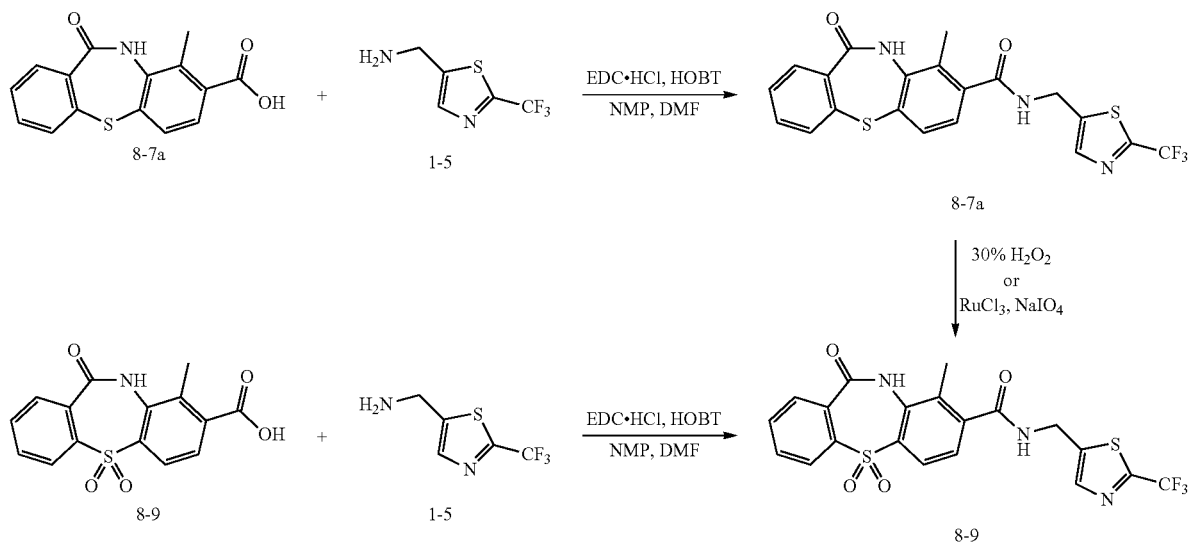 [SMILES: Cc1c(C(=O)O)ccc2c1NC(=O)c1ccccc1S2 ; NCc1cnc(C(F)(F)F)s1 ; Cc1c(C(=O)NCc2cnc(C(F)(F)F)s2)ccc2c1NC(=O)c1ccccc1S2 ; Cc1c(C(=O)O)ccc2c1NC(=O)c1ccccc1S2(=O)=O ; NCc1cnc(C(F)(F)F)s1 ; Cc1c(C(=O)NCc2cnc(C(F)(F)F)s2)ccc2c1NC(=O)c1ccccc1S2(=O)=O]

Route 1 Step 1

Compound 8-7a was obtained from compound 8-7 by hydrolysis of the methyl ester. Following amide formation procedure described in Example 4 and substituting acid 3-7 with 8-7a, compound 9-1 was obtained. $^1$H-NMR (DMSO-$d_6$, 500 MHz): δ 10.24 (s, 1H), 9.15 (t, J=5.8 Hz, 1H), 8.04 (s, 1H), 7.67-7.63 (m, 1H), 7.54-7.49 (m, 2H), 7.48-7.41 (m, 2H), 7.11 (d, J=7.8 Hz, 1H), 4.69 (d, J=5.8 Hz, 2H), 2.28 (s, 3H); LCMS: m/z 448.1 [M–H]$^-$.

Route 1 Step 2

Subjecting a sample of 9-1 to oxidative conditions described in Example 3 (Method A or Method B) led to compound 9-2. $^1$H-NMR (DMSO-$d_6$, 400 MHz): δ 10.86 (br s, 1H), 9.30 (t, J=5.8 Hz, 1H), 8.06 (s, 1H), 7.95-7.84 (m, 4H), 7.80 (td, J=7.5, 1.4 Hz, 1H), 7.38 (d, J=8.2 Hz, 1H), 4.72 (d, J=5.6 Hz, 2H), 2.31 (s, 3H); LCMS: m/z: 481.1 [M+H]$^+$.

Compound 9-2 was obtained alternatively produced by reaction a sample of acid 8-9 with amine 1-5 using the amide coupling conditions described in Example 4.

Example 10: N-((2-ethylthiazol-5-yl)methyl)-11-oxo-10,11-dihydrodibenzo[b,f][1,4]thiazepine-8-carboxamide 5,5-dioxide (10)

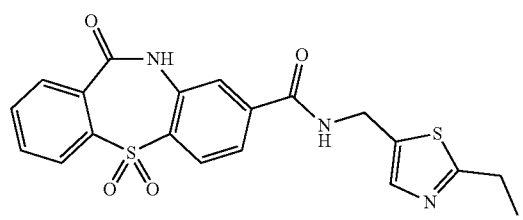 [SMILES: CCc1ncc(CNC(=O)c2ccc3c(c2)NC(=O)c2ccccc2S3(=O)=O)s1]

The title compound 10 was obtained alternatively produced by reaction a sample of acid 3-7 with amine 2-7 using the amide coupling conditions described in Example 4. $^1$H-NMR (DMSO-$d_6$, 500 MHz): δ 11.52 (s, 1H), 9.40 (t, J=5.8 Hz, 1H), 8.04 (d, J=8.4 Hz, 1H), 7.97 (t, J=8.4 Hz, 2H), 7.90 (t, J=7.1 Hz, 1H), 7.87-7.81 (m, 2H), 7.78 (d, J=8.1 Hz, 1H), 7.53 (s, 1H), 4.58 (d, J=5.8 Hz, 2H), 2.89 (q, J=7.5 Hz, 2H), 1.23 (t, J=7.5 Hz, 3H); LCMS: m/z: 427.9 [M=H]$^+$.

Example 11: 11-oxo-N-((2-(trifluoromethyl)thiazol-5-yl)methyl)-10,11-dihydrodibenzo[b,f][1,4]thiazepine-8-carboxamide 5-oxide (11-3)

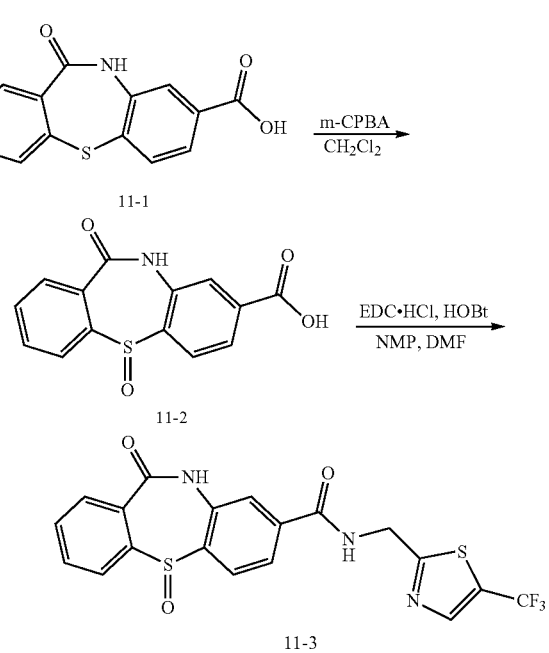

Step 1: Synthesis of 11-oxo-10, 11-dihydrodibenzo[b,f] [1, 4] thiazepine-8-carboxylic Acid 5-oxide (89)

To a stirring solution of 11-1 (obtained similarly by following procedures described in the Examples 3, 5, 7, 8) (2.5 g, 9.21 mmol) in $CH_2Cl_2$ (50 mL) under inert atmosphere was added m-chloro perbenzoic acid (1.59 g, 9.21 mmol) at RT and stirred for 48 h. The reaction was monitored by TLC; after completion of the reaction, the reaction mixture was the volatiles were removed in vacuo to obtain the crude. The crude was triturated with 10% MeOH/$CH_2Cl_2$ (2×5 mL), isopropanol (10 mL) to afford compound 11-2 (2.3 g, 87%) as white solid. TLC: 10% MeOH/$CH_2Cl_2$+0.05 mL $CH_3COOH$ ($R_f$: 0.4); $^1H$ NMR (DMSO-$d_6$, 500 MHz): δ 13.36 (br s, 1H), 11.08 (s, 1H), 7.96 (d, J=7.8 Hz, 1H), 7.92-7.87 (m, 1H), 7.85-7.66 (m, 3H), 7.63 (t, J=7.8 Hz, 1H), 7.53 (t, J=7.8 Hz, 1H);

Step 2

11-oxo-N-((2-(trifluoromethyl)thiazol-5-yl)methyl)-10,11-dihydrodibenzo[b,f][1,4]thiazepine-8-carboxamide 5-oxide was prepared by coupling 11-1 and amine 1-5 following procedures described in Example 4. $^1$H-NMR (DMSO-$d_6$, 400 MHz): δ 11.06 (s, 1H), 9.46 (t, J=5.8 Hz, 1H), 8.05 (s, 1H), 7.88 (dd, J=8.2, 1.5 Hz, 1H), 7.84-7.77 (m, 2H), 7.76-7.68 (m, 3H), 7.63 (td, J=7.5, 1.3 Hz, 1H), 4.72 (d, J=5.6 Hz, 2H); LCMS: m/z: 451.9 [M+H]$^+$.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A process for preparing a compound represented by Formula I:

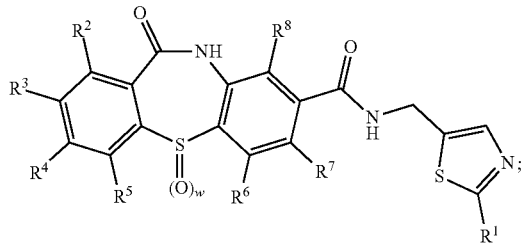

Formula I wherein w is 0, 1, or 2;

$R^1$ is selected from the group consisting of $C_{1-6}$alkyl (optionally substituted with one, two or three halogens), phenyl, and a monocyclic 5-6 membered ring system containing one or more heteroatoms selected from the group consisting of nitrogen, oxygen, and sulfur; wherein phenyl and the monocyclic 5-6 membered ring containing one or more heteroatoms may optionally be substituted with one or more substituents each independently selected from $R^{11}$;

$R^{11}$ is selected from the group consisting of hydrogen, halogen, cyano, $C_{1-6}$alkyl, $C_{1-6}$alkoxy, and —S(O)$_w$—$C_{1-6}$alkyl (wherein w is 0, 1 or 2);

$R^2$, $R^3$, $R^4$, $R^5$, $R^6$, $R^7$, and $R^8$ are each independently selected from the group consisting of hydrogen, halogen, $C_{1-6}$alkyl, and $C_{1-6}$alkoxy; wherein $C_{1-6}$alkyl and $C_{1-6}$alkoxy may be optionally substituted with one, two, three or more substituents each independently selected from the group consisting of halogen, hydroxyl, and $C_{1-6}$alkoxy;

comprising:

amidating a compound of Formula II:

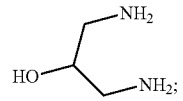

Formula II to provide a compound of Formula III:

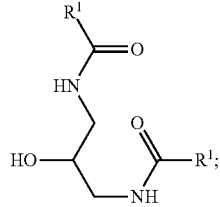

Formula III oxidizing the compound of Formula III to provide a compound of Formula IV:

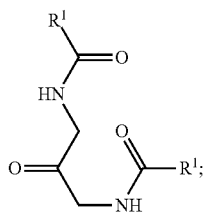

Formula IV cyclizing the compound of Formula IV to provide a thiazole compound of Formula V:

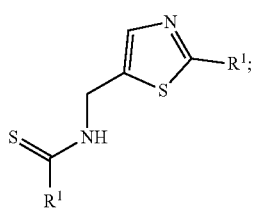

Formula V hydrolyzing the compound of Formula V to provide a compound of Formula VI:

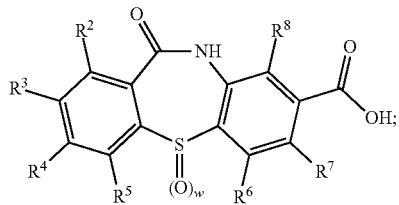

Formula VI and coupling the compound of Formula VI with a tricyclic compound of Formula VII:

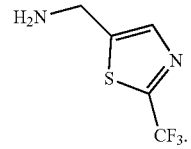

Formula VII wherein w is 0, 1 or 2;
to provide the compound of Formula I.

2. The process of claim 1, wherein amidating the compound of Formula II comprises contacting the compound of Formula II with an amine base and an acylating agent.

3. The process of claim 1, wherein the acylating agent is an acid anhydride or an acid chloride.

4. The process of claim 1, wherein the acylating agent is trifluoroacetic anhydride.

5. The process of claim 1, wherein the amine base is triethylamine.

6. The process of claim 1, wherein oxidizing the compound of Formula III comprises contacting the compound of Formula III with a chromium-based oxidizing reagent.

7. The process of claim 6, wherein the chromium-based oxidizing reagent is Jones reagent.

8. The process of claim 1, wherein cyclizing the compound of Formula IV comprises contacting the compound of Formula IV with a thionating reagent.

9. The process of claim 8, wherein the thionating reagent is phosphorus pentasulfide.

10. The process of claim 1, wherein hydrolyzing the compound of Formula V comprises contacting the compound of Formula V with an aqueous amine base.

11. The process of claim 10, wherein the aqueous amine base is aqueous methylamine.

12. The process of claim 1, wherein coupling the compound of Formula VI with the compound of Formula VII is conducted in the presence of a coupling agent.

13. The process of claim 12, wherein the coupling agent is hydroxybenzotriazole/ethyl-(N',N'-dimethylamino)propylcarbodiimide hydrochloride.

14. The process of claim 1, wherein $R^2$, $R^3$, $R^4$, $R^5$, $R^6$, $R^7$, and $R^8$ are each independently selected from the group consisting of hydrogen, fluoride, chloride, methyl, and methoxy.

15. The process of claim 1, wherein $R^1$ is trifluoromethyl.

16. The process of claim 1, wherein the compound of Formula VI is:

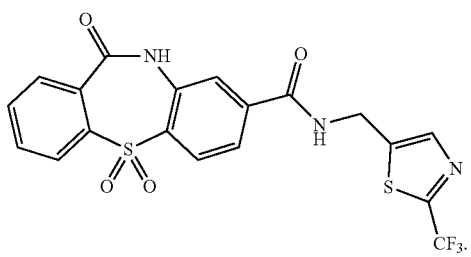 [SMILES: O=C(NCc1cnc(C(F)(F)F)s1)c1ccc2c(c1)NC(=O)c1ccccc1S2(=O)=O]

17. The process of claim 1, wherein the compound of Formula I is:

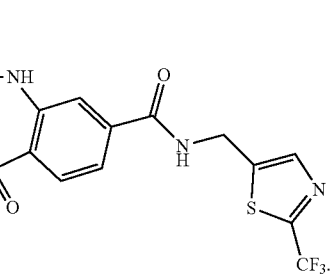

* * * * *